United States Patent
Riedel et al.

(10) Patent No.: US 7,066,940 B2
(45) Date of Patent: *Jun. 27, 2006

(54) SURGICAL INSTRUMENT WITH ROTARY CUTTING MEMBER AND QUICK RELEASE COUPLING ARRANGEMENT

(75) Inventors: Danny C. Riedel, Weatherford, TX (US); Durrell G. Tidwell, Burleson, TX (US); Bryan David Simmons, Flower Mound, TX (US); Larry Dale Estes, North Richland Hills, TX (US); Allen P. Hilton, Arlington, TX (US); Rex Wesley Shores, The Colony, TX (US); John K. Henderson, Flower Mound, TX (US); James Q. Spitler, Cleburne, TX (US); Michelle L. Walker, Lewisville, TX (US); Dana A. Eskridge, Ojai, CA (US); Dennis L. Foster, Ojai, CA (US); Douglas W Haight, Camarillo, CA (US); Laura A. Kriese, Ventura, CA (US); Stephen G Savage, Oxnard, CA (US)

(73) Assignee: Medtronic, Inc., Minneapolis, MN (US)

( * ) Notice: Subject to any disclaimer, the term of this patent is extended or adjusted under 35 U.S.C. 154(b) by 589 days.

This patent is subject to a terminal disclaimer.

(21) Appl. No.: 10/102,762

(22) Filed: Mar. 21, 2002

(65) Prior Publication Data
US 2002/0151902 A1    Oct. 17, 2002

Related U.S. Application Data

(60) Provisional application No. 60/277,639, filed on Mar. 21, 2001.

(51) Int. Cl.
*A61B 17/00* (2006.01)

(52) U.S. Cl. ............................ 606/79; 606/167

(58) Field of Classification Search ............... 606/80, 606/81, 167, 170, 79, 169, 171, 172, 179, 606/180; 433/126, 127, 128, 165, 166; 408/226; 279/75
See application file for complete search history.

(56) References Cited

U.S. PATENT DOCUMENTS 929,563 A * 7/1909 Coulter ................... 408/95
2,807,473 A   9/1957 Kiehne (Continued)

FOREIGN PATENT DOCUMENTS

CH    375 484    4/1964

(Continued)

OTHER PUBLICATIONS

European Search Report, completed on Jun. 21, 2004, EP application No. EP 03 07 7262.

*Primary Examiner*—David O. Reip
(74) *Attorney, Agent, or Firm*—Haynes and Boone, LLP

(57) ABSTRACT

A surgical instrument for the dissection of bone and other tissue includes a spindle, a dissection tool and a male member carried by the spindle. The spindle includes a cavity. The dissection tool is releasably received in the cavity. The dissection tool extends along an axis and includes a first end and a second end with the first end having a cutting element and a second end having a generally cylindrical cross-section and a centrally located aperture partially extending along the axis. The male member is carried by the spindle and extends into the aperture of the dissection tool.

31 Claims, 14 Drawing Sheets

U.S. PATENT DOCUMENTS

| | | |
|---|---|---|
| 4,021,920 A * | 5/1977 | Kirschner et al. ............ 433/82 |
| 4,699,550 A | 10/1987 | Baker |
| 5,222,956 A | 6/1993 | Waldron |
| 5,330,480 A | 7/1994 | Meloul et al. |
| 5,347,988 A | 9/1994 | Hori |
| 5,366,374 A * | 11/1994 | Vlassis ...................... 433/165 |
| 5,380,333 A | 1/1995 | Meloul et al. |
| 5,490,683 A | 2/1996 | Mickel et al. |
| 5,505,737 A | 4/1996 | Gosselin et al. |
| 5,569,256 A | 10/1996 | Vaughn et al. |
| 5,601,560 A | 2/1997 | Del Rio et al. |
| 5,630,818 A | 5/1997 | Del Rio et al. |
| 5,741,263 A | 4/1998 | Umber et al. |
| 5,779,404 A | 7/1998 | Jore |
| 5,782,836 A | 7/1998 | Umber et al. |
| 5,833,704 A | 11/1998 | McCombs et al. |
| 5,888,200 A | 3/1999 | Walen |
| 5,893,851 A | 4/1999 | Umber et al. |
| 5,904,687 A | 5/1999 | Del Rio et al. |
| 5,928,238 A | 7/1999 | Scarborough et al. |
| 5,928,241 A | 7/1999 | Menut et al. |
| 5,941,891 A | 8/1999 | Walen |
| 5,989,257 A | 11/1999 | Tidwell et al. |
| 5,993,453 A | 11/1999 | Bullara et al. |
| 5,993,454 A | 11/1999 | Longo |
| 6,033,408 A | 3/2000 | Gage et al. |
| 6,062,575 A | 5/2000 | Mickel et al. |
| 6,209,886 B1 | 4/2001 | Estes et al. |
| 6,270,087 B1 | 8/2001 | Mickel et al. |
| RE37,358 E | 9/2001 | Del Rio et al. |
| 2002/0058958 A1 | 5/2002 | Walen |

FOREIGN PATENT DOCUMENTS

| | | |
|---|---|---|
| WO | WO 92/08410 | 5/1992 |
| WO | WO 96/10962 | 4/1996 |
| WO | WO 02/076308 | 10/2002 |

* cited by examiner

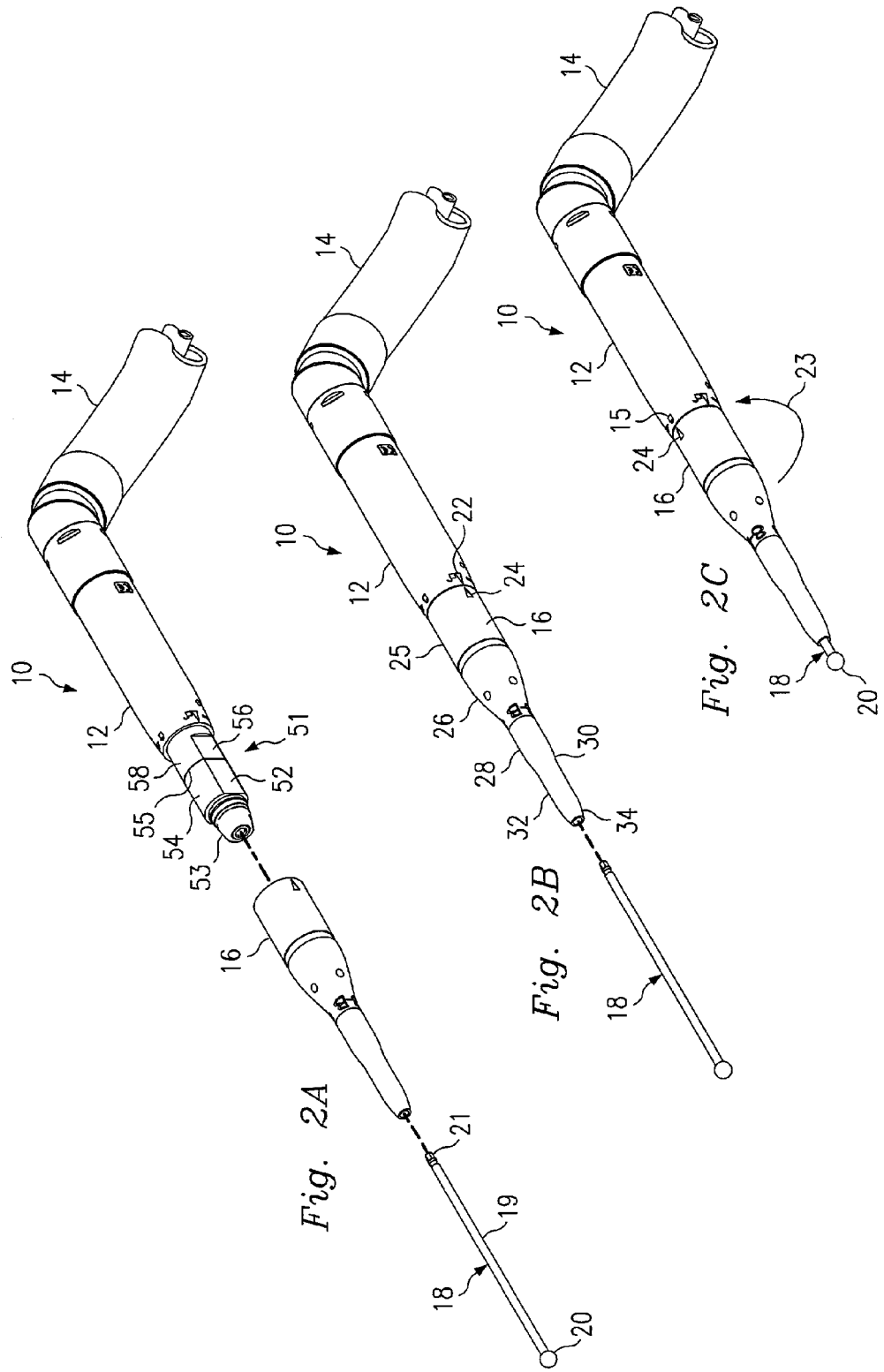

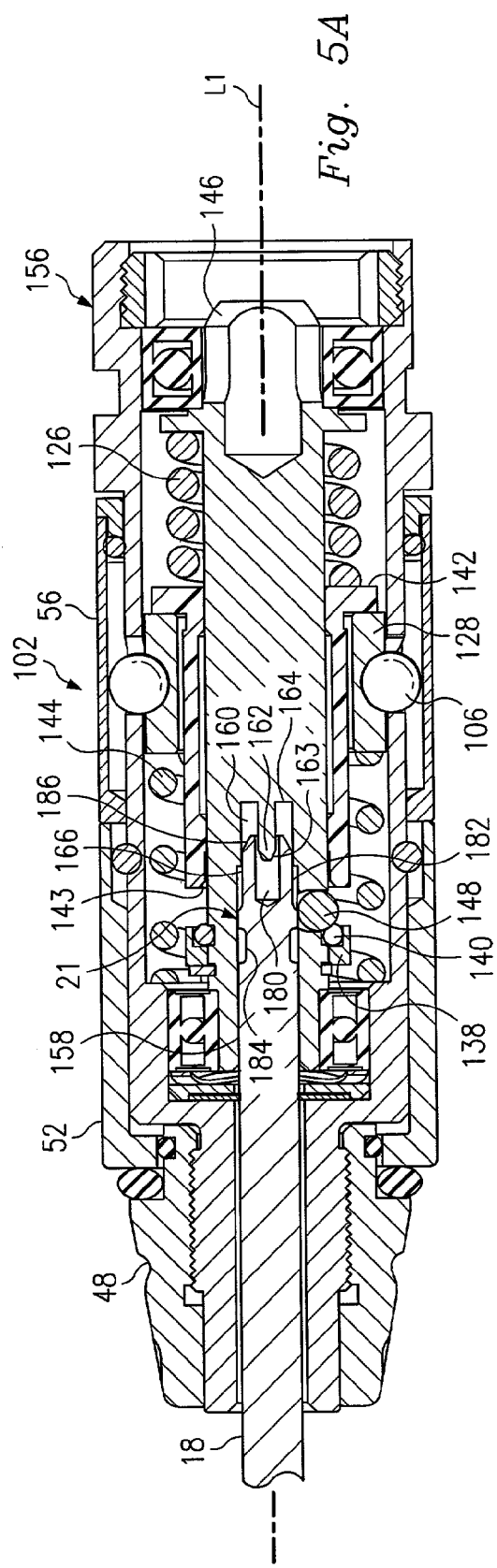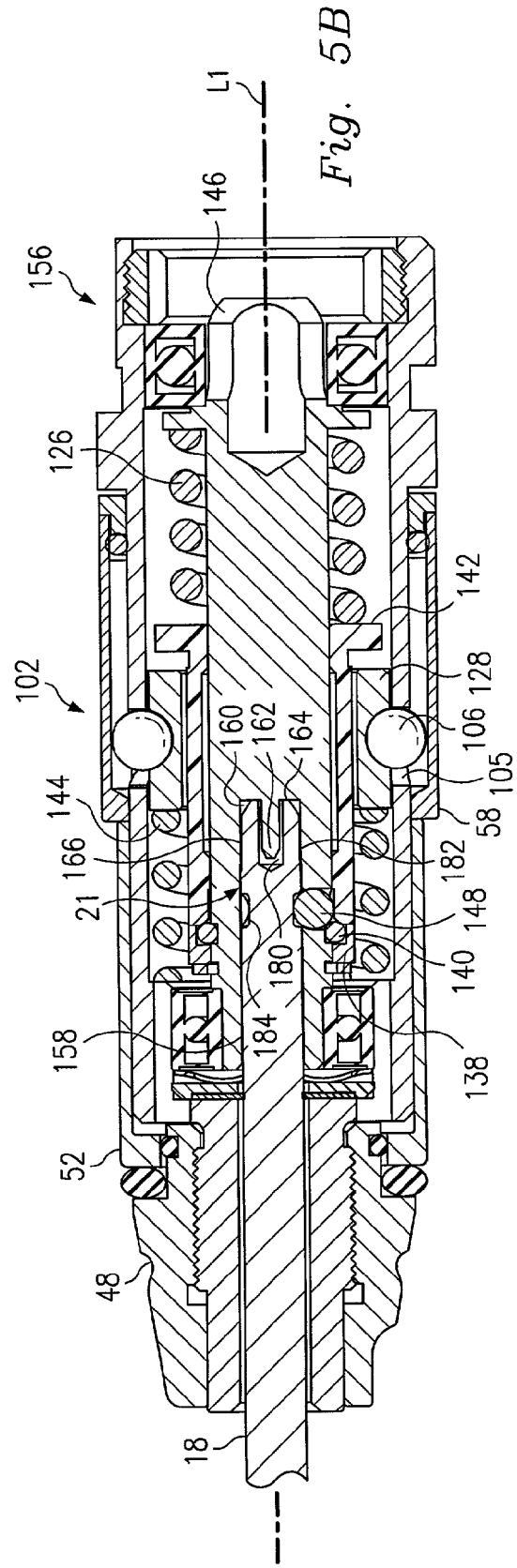
Fig. 5A
Fig. 5B

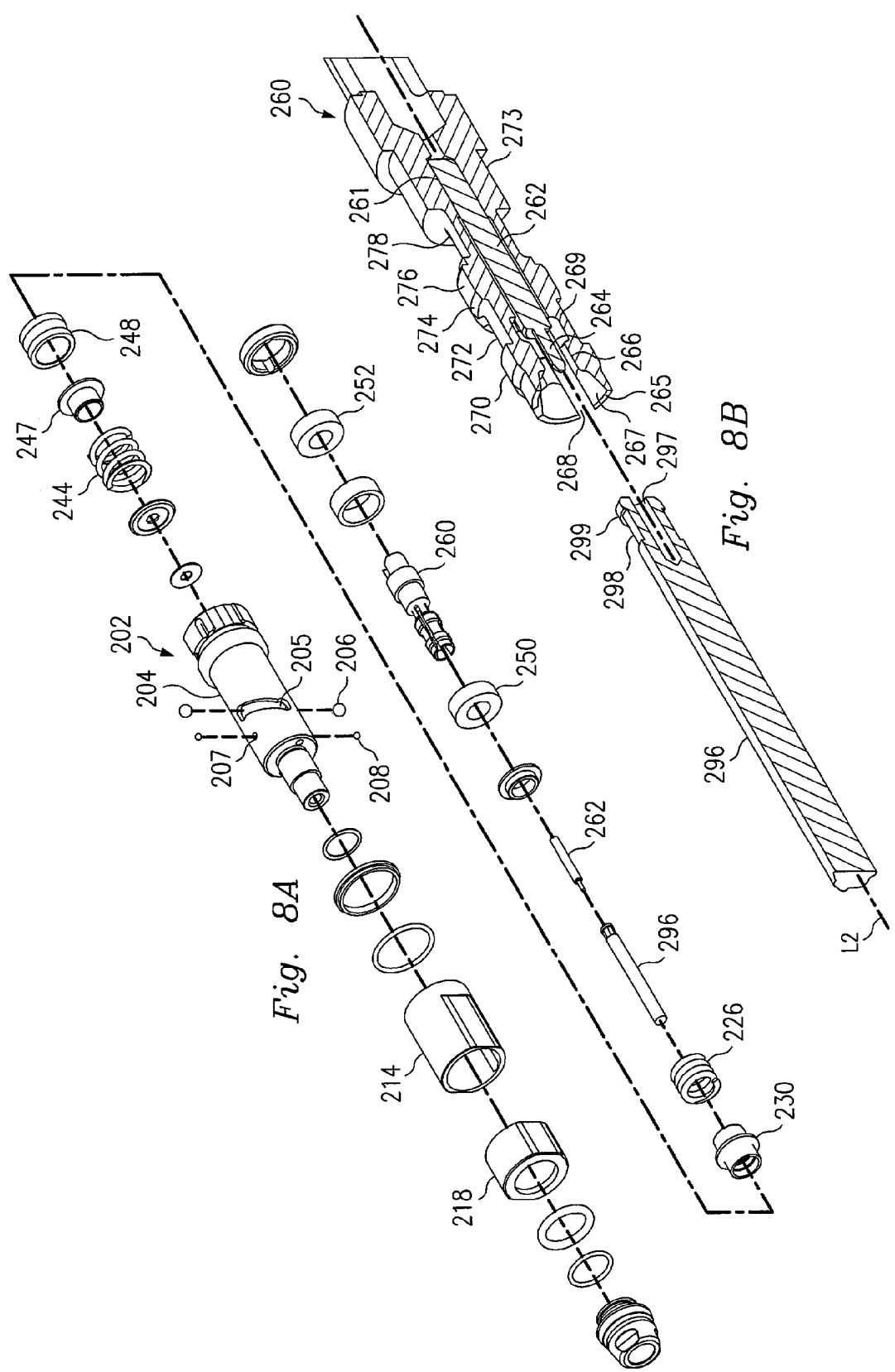

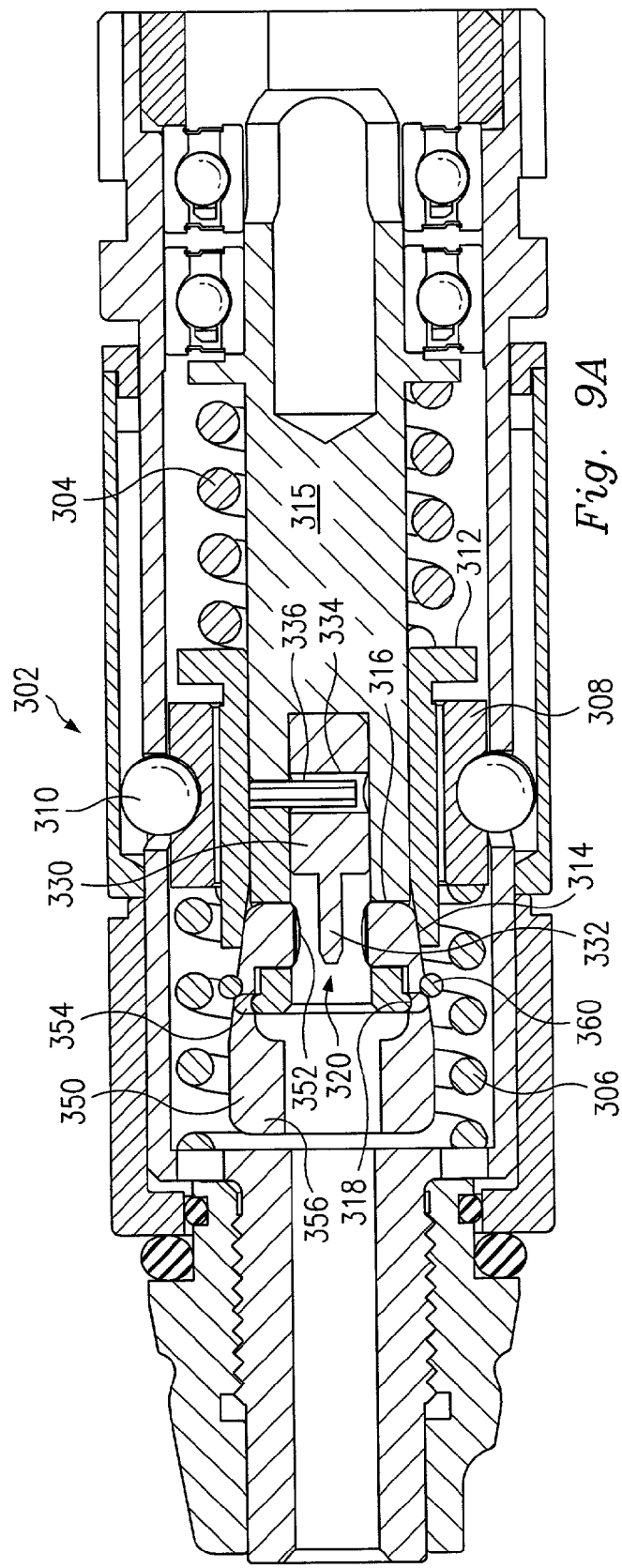
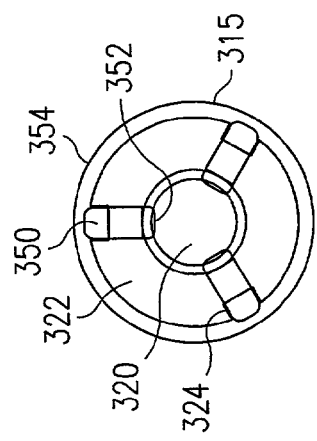
Fig. 9A
Fig. 9B

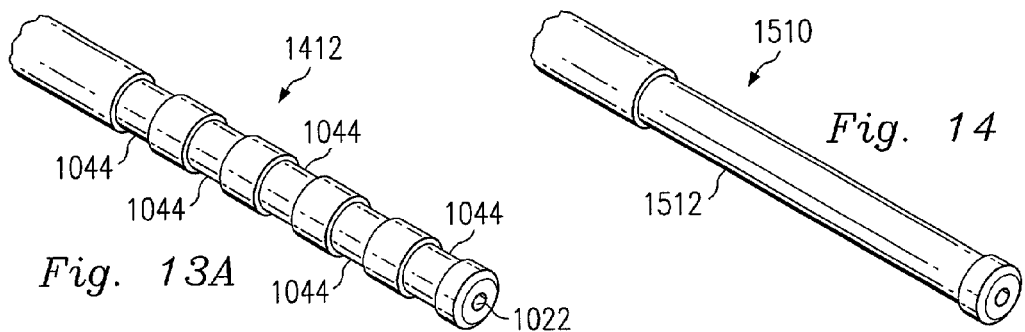
Fig. 13A
Fig. 14
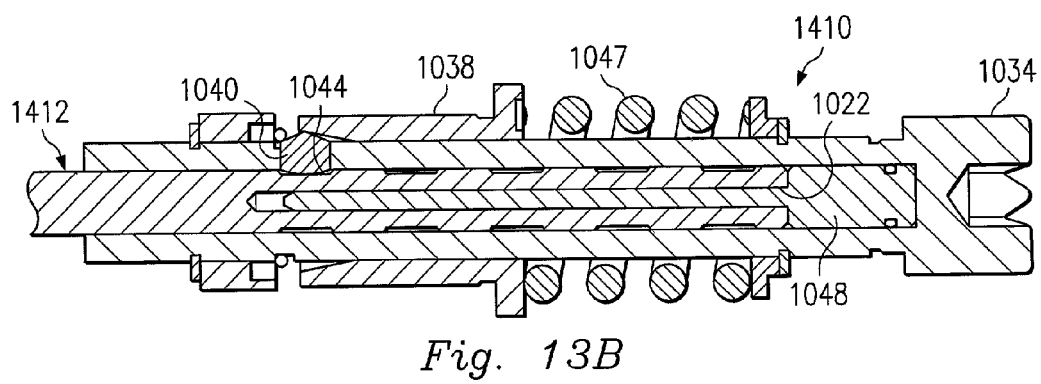
Fig. 13B
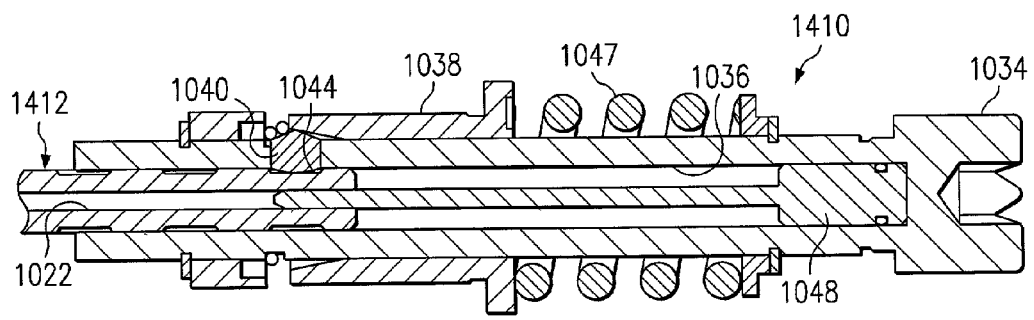
Fig. 13C

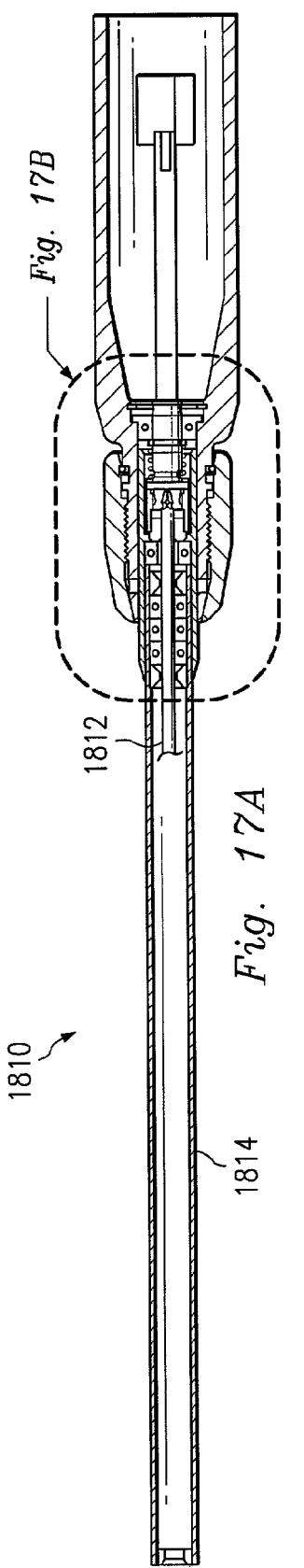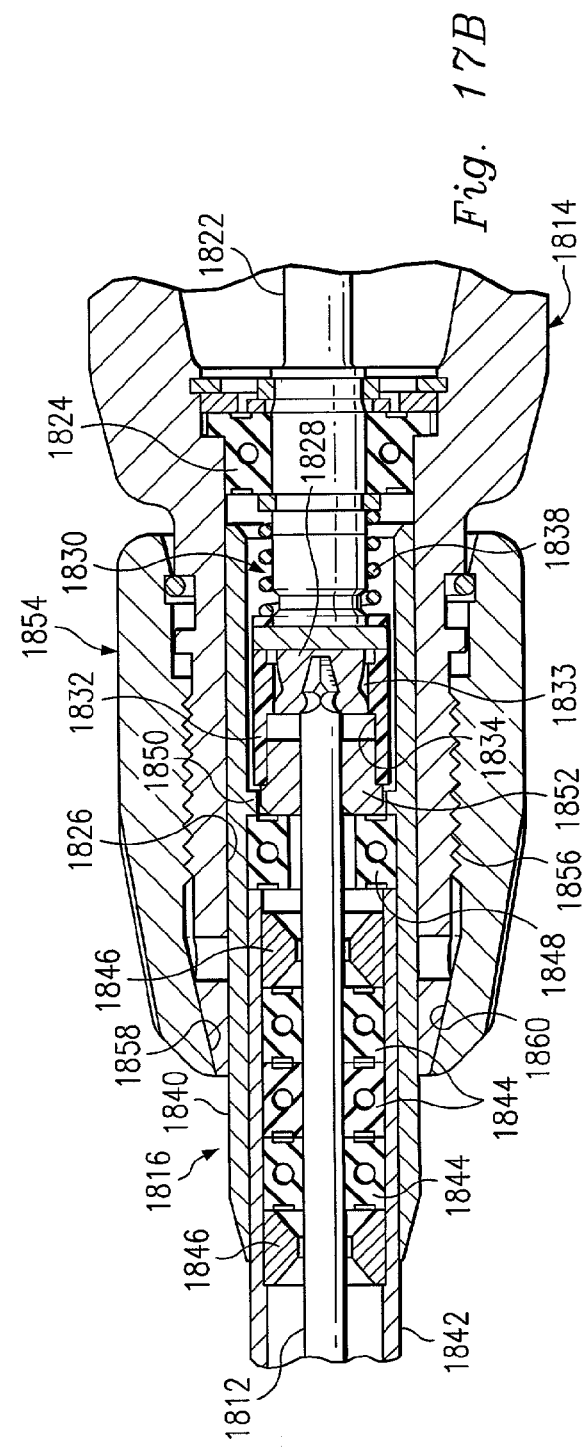

SURGICAL INSTRUMENT WITH ROTARY CUTTING MEMBER AND QUICK RELEASE COUPLING ARRANGEMENT

CROSS-REFERENCE TO RELATED APPLICATION

This invention claims priority to U.S. Provisional Application No. 60/277,639, filed Mar. 21, 2001, incorporated herein by reference.

FIELD OF THE INVENTION

The present invention generally relates to surgical instruments for use in the dissection of bone and other tissue. More particularly, the present invention relates to a dissection tool and a quick release coupling arrangement for a surgical instrument.

BACKGROUND OF THE INVENTION

In various surgical procedures, it is necessary to dissect bone or other tissue. Many conventional surgical instruments used for the dissection of bone or other tissue employ pneumatic or electrical motors to rotate a cutting element. In their most basic form, such surgical instruments comprise a motor portion having a rotary shaft, a dissection tool having a cutting or abrading element that is rotated by the rotating shaft of the motor, and a coupling arrangement for connecting the dissection tool to a spindle or collet of the rotary shaft. The spindle or collet of the rotary shaft is usually housed within a base that is attached to the motor.

Because it is frequently necessary to replace the dissection tool, it is also known in the art to use a quick release coupling to secure the dissection tool to the surgical instrument. An example of such a quick release coupling is shown and described in commonly assigned U.S. Pat. No. 5,505,737 entitled "Quick Release Coupling For A Dissecting Tool." The coupling device shown in U.S. Pat. No. 5,505,737 includes a spindle attachment which is secured to a spindle of a surgical instrument. The spindle attachment has a shaft engagement portion for engaging a shaft of the dissection tool. The shaft engagement portion of the spindle attachment is provided with apertures that terminate within a central bore of the engagement portion through which the shaft of the dissection tool extends.

Surrounding the spindle attachment is a cylindrical sleeve having a contact surface that engages several spherical locking members located within the apertures of the shaft engagement portion of the spindle attachment. A sleeve engagement member is coupled to the base of the surgical instrument and is movable between retracted and extended positions.

As the sleeve engagement member is moved between the retracted and extended positions, it causes the sleeve of the surgical instrument to be moved between an engaged and disengaged position with respect to the dissection tool. When the sleeve is moved to the engaged position, the contact surface of the sleeve forces the spherical locking members inward toward the central bore of the spindle attachment where the locking members contact the shaft of the dissection tool, thereby preventing removal of the dissection tool from the surgical instrument. When the sleeve is moved to the disengaged position in which the spherical locking members are allowed to retract within the apertures, the dissection tool is able to be removed from the socket.

While known surgical tools including replaceable dissection tools have proven to be acceptable for their intended applications, it remains desirable to further advance the pertinent art. For example, due to the high speed rotating action of the dissection tool, a need exists in the art for more precise alignment of the dissection tool within the surgical instrument. Further, in past designs, the coupling mechanism has not included means to limit the acceptance of non-approved tool shafts. Specifically, non-approved or qualified tool shafts may suffer from a number of problems. End users may improperly select a tool shaft of the incorrect strength for a given length, select the incorrect diameter, or attempt to utilize the incorrect cutting head configuration based on the motor design. Such variations in the tool shaft can result in damage to the motor coupling assembly and supporting bearings in the attachment housing, result in extreme cutting tip flail at high speed potentially causing injury to a patient and stressing the tool shaft with the possibility for breakage. Additionally, a need exists in the pertinent art for an improved surgical tool which permits telescoping of the dissection tool relative to a fixed sleeve.

SUMMARY OF THE INVENTION

In one particular embodiment, the surgical instrument includes a rotary spindle or shaft having a cavity, as well as a dissection tool releasably received within the cavity. The dissection tool extends along a longitudinal axis and includes a first end and a second end. The first end of the dissection tool includes a cutting element, and the second end a centrally located bore partially extending inwardly along the longitudinal axis. A centrally located pin is carried by the spindle and extends into the bore of the dissection tool in a coupled engagement.

In another particular embodiment, the surgical instrument includes a fixed sleeve and a dissection tool rotatably disposed within and partially extending from the sleeve. The surgical tool additionally includes a coupling arrangement for releasably engaging the dissection tool. The dissection tool is translatable along its axis and relative to the fixed sleeve between a retracted position and an extended position.

In yet another particular embodiment, the surgical instrument of the present invention includes a dissection tool, a housing, and a coupling arrangement carried by the housing releasably engaging the dissection tool. The dissection tool includes a reduced diameter portion. The coupling arrangement includes a plurality of locking members engaging the reduced diameter portion. In a preferred aspect, the reduced diameter portion is defined by a plurality of planar sides. Still more preferably, the number of planar sides of the plurality of planar sides is equally divisible by the number of locking members of the plurality of locking members.

A potential advantage of the present invention is the provision of a surgical instrument for the dissection of bone and other tissue in which the dissection tool is precisely centered within the surgical instrument.

Another potential advantage of the present invention is the provision of a surgical instrument for the dissection of bone and other tissue which inhibits attachment of dissection tools that are not designed for operation in the surgical instrument. Still a further aspect of the present invention is the provision of a dissection tool having a coupling end with drive surfaces and at least one longitudinal alignment surface. In one preferred embodiment of the invention, the alignment surface extends internally to the drive surface. In another preferred embodiment the alignment surface is disposed on the external surface of the dissection tool.

Another potential advantage of the present invention is the provision of a surgical instrument for the dissection of bone and other tissue in which a dissection tool is more securely attached to the surgical instrument to prevent unwanted movement of the distal end of the dissection tool.

Another potential advantage of the present invention is the provision of a surgical instrument for the dissection of bone and other tissue in which a tactile feeling is generated upon insertion of the dissection tool into the surgical instrument so as to provide an indication to the user of proper engagement of the dissection tool.

Another potential advantage of the present invention is the provision of a surgical instrument for the dissection of bone and other tissue which includes a rotationally fixed sleeve and a rotatable dissection tool disposed in the sleeve and translatable relative to the sleeve between a retracted position and an extended position.

Still a further object of the present invention is the provision of a tool shaft and quick release coupler that may provide three dimensions of alignment during a coupling procedure. The assembly may provide transverse, longitudinal and rotational alignment in relation to the longitudinal axis.

In yet a further aspect of the present invention, a tool member is provided that includes an internal engagement portion and a cooperating external engagement portion. In a preferred aspect, the internal engagement portion permits axial alignment by receiving a projection and the external engagement portion is adapted to receive torque transmission from a surrounding coupler. Still more preferably, the internal engagement portion and the external engagement portion have axially overlapping sections over at least a portion of their length.

In yet an additional aspect of the present invention, the external surface of the attachment housing is configured with multiple tapers to increase tool tip visibility.

Still further, another preferred aspect of the present invention is the provision of tactile feedback upon the engagement of the attachment housing with the motor housing. In a preferred aspect, the attachment housing is joined to the motor housing with an interference fit. In a further preferred aspect, the engagement between the motor housing and attachment housing is confirmed by an audible sound.

In another aspect, the present invention provides quick release coupling members to engage a dissection tool.

In still a further aspect, the present invention provides dissection tools with non-perpendicular driving surfaces.

Additional advantages and features of the present invention will become apparent from the following description and appended claims, taken in conjunction with the accompanying drawings.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 2A is a partially exploded perspective view of a surgical dissection tool according to the present invention.

FIG. 2B is a partially exploded perspective view of a surgical dissection tool according to the present invention.

FIG. 2C is an assembled perspective view of the surgical dissection tool of FIG. 2A.

FIG. 5A is a partial cross-sectional side view of a portion of the surgical dissection tool of FIG. 3 rotated 90° illustrating the unlocked position.

FIG. 5B is a partial cross-sectional side view of the surgical dissection tool of FIG. 5A with a portion thereof rotated to illustrate the locked position.

FIG. 8A is an exploded perspective view of a portion of a surgical dissection tool according to still another aspect of the present invention.

FIG. 8B is a partial cross-sectional perspective view of a portion of FIG. 8A.

FIG. 9A is a partial cross-sectional side view of a potion of a surgical dissection tool according to another aspect of the present invention.

FIG. 9B is a partial end view of FIG. 9A.

FIG. 13A is a perspective view of a proximal end of a dissection tool of a surgical instrument for the dissection of bone and other tissue according to the teachings of still a further embodiment of the present invention.

FIG. 13B is a cross-sectional of a portion of a surgical instrument for the dissection of bone and other tissue according to the teachings of FIG. 13A, the dissection tool shown in a fully retracted position.

FIG. 13C is a cross-sectional view similar to FIG. 13B illustrating the dissection tool in a fully extended position.

FIG. 14 is a perspective view of a proximal end of a dissection tool of a surgical instrument for the dissection of bone and other tissue according to the teachings of a further preferred embodiment of the present invention.

FIG. 17A is a partial cross-sectional view of a portion of a surgical instrument for the dissection of bone and other tissue according to the teachings of another preferred embodiment of the present invention.

FIG. 17B is an enlarged cross-sectional view of FIG. 17A, illustrating the closure member in a clamped position securing the dissection tool to the input shaft.

DETAILED DESCRIPTION OF THE PREFERRED EMBODIMENTS

The following description of the preferred embodiments is merely exemplary in nature and is in no way intended to limit the invention, its application, or uses.

Figure 1:
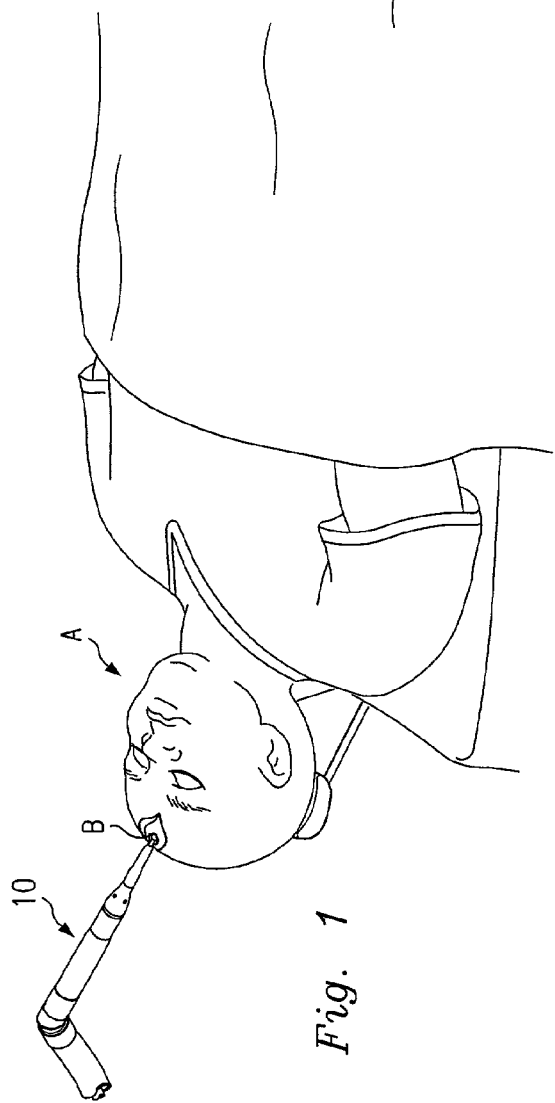
FIG. 1 is an illustration of a surgical dissection tool according to the present invention used in a human patient.

Referring now to FIG. 1, there is shown a human patient A undergoing a neurological operation. As is common practice, access to the brain or other neurological structures often requires delicate dissection of bone and other tissues B to gain access. By way of example, dissection tool assembly 10 in accordance with one aspect of the present invention is shown being utilized to dissect a portion of patient A's bone and other tissue B adjacent to the surgical access site.

Referring now to FIGS. 2A–2C, a dissection tool assembly 10 for the dissection of bone or other tissue is illustrated. Dissection tool assembly 10 includes a motor housing 12, coupled to air supply and hose assembly 14 that supplies pressurized air to the motor and vents the low pressure exhaust air away from the surgical site. Dissection tool assembly 10 further includes an attachment housing 16 and a dissection tool 18. As shown in FIG. 2A, the distal portion 51 of motor housing 12 includes a tapered leading portion 53 and a Double D connection region. The Double D region comprises a pair of opposed and substantially parallel planar portions interrupting the cylindrical body to define two opposed substantially parallel cylindrical portions. These portions are separated by junction 55 into a fixed segment having cylindrical portion 54 and flat portion 52, and a movable segment having cylindrical portion 58 and flat portion 56.

Figure 3:
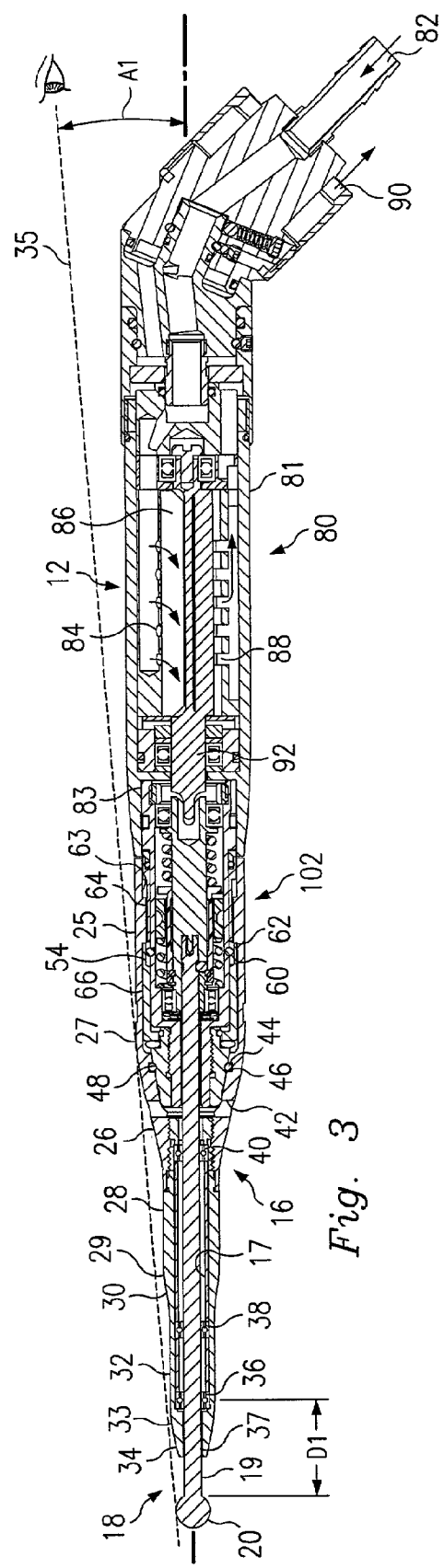
FIG. 3 is a partial cross-sectional side view of the surgical dissection tool of FIG. 2C.
Figure 4:
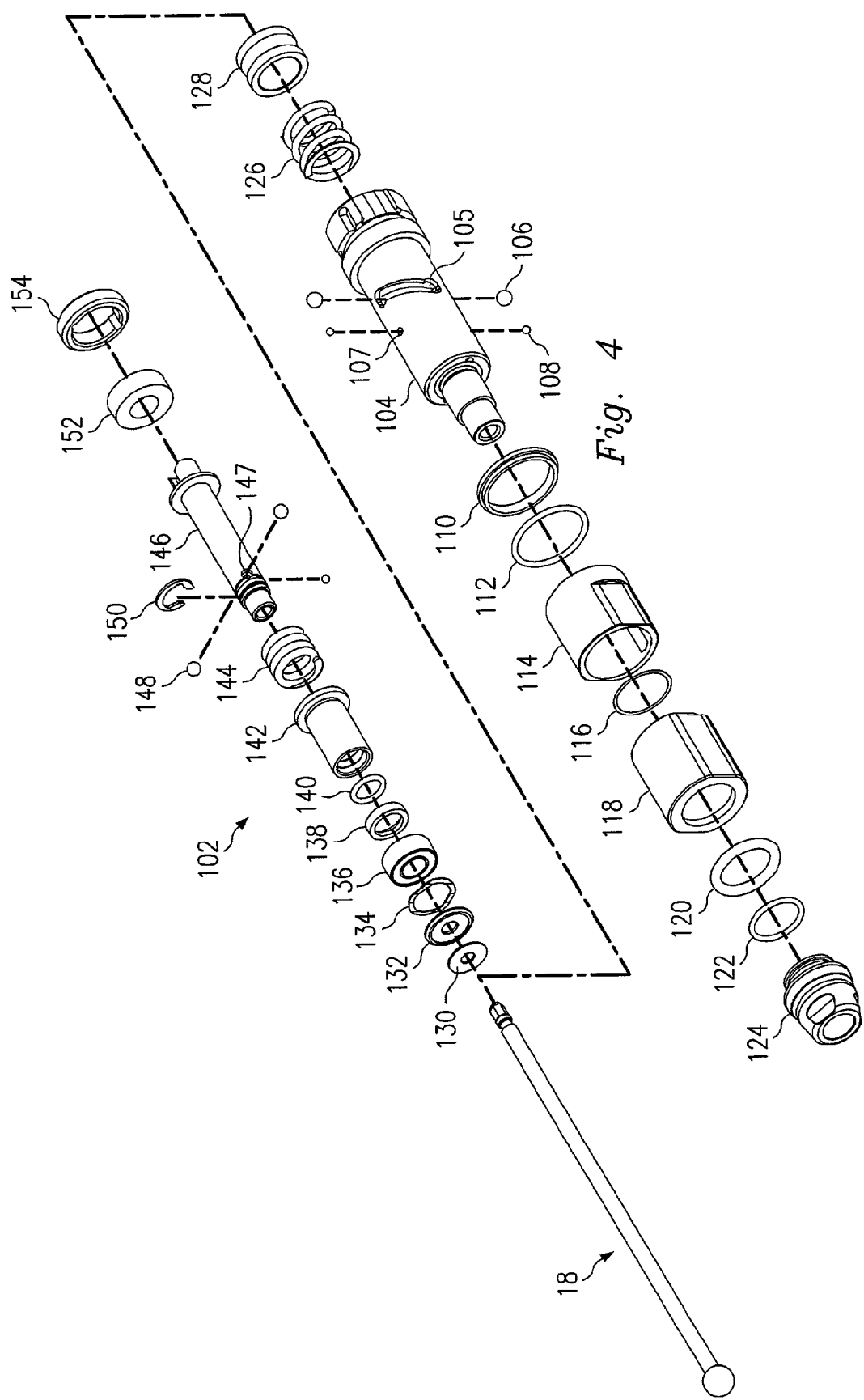
FIG. 4 is an exploded perspective view of a portion of the surgical dissection tool of FIG. 3.

Referring now to FIGS. 2B and 3, attachment housing 16 includes an internal cavity 63 adapted and configured to engage distal portion 51 of motor housing 12. In an initial position with first cylindrical portion 25 substantially abutting motor housing 12, attachment indicator mark 24 is in substantial alignment with unlocked indicator mark 22 on the motor housing. In this position, dissection tool 18 may be inserted into attachment housing 16 and be received in a coupling assembly (described later) within motor housing 12. Referring now to FIG. 2C, with dissection tool 18 inserted within attachment housing 16 and engaged in the coupling of the motor housing 12 (see FIGS. 3–5B), attachment housing 16 may be rotated in the direction of arrow 23 with respect to motor housing 12. Movement in this direction moves attachment indicator marking 24 into substantial alignment with the locked indicator marking 15 on motor housing 12. As described further herein, such movement also operates the coupling assembly to lock dissection tool 18 into driving engagement with the internal motor.

In a preferred aspect of the present invention, attachment housing 16 is adapted to engage the distal portion 51 of motor housing 12 in an interference fit. Further, attachment housing 16 and distal portion 51 are configured to provide the user with tactical feedback indicating positive engagement. More specifically, internal cavity 63 includes an internal annular groove 46 carrying an O-ring 44. Distal portion 51 defines an external annular groove 48 adapted to receive a portion of O-ring 44. Thus, it will be understood that as attachment housing 16 is advanced over distal portion 51, O-ring 44 will be slightly compressed into grove 46 as it engages tapered front end 53 to an expanded inner diameter. When O-ring 44 is positioned over annular groove 48, the compressed O-ring 44 will quickly relax into a smaller inner diameter shape engaging annular groove 48 providing the user with a tactile sensation. Preferably such tactile sensation will include both a vibration and auditory signal, indicating that the attachment is in the proper position on motor housing 12. While the movement of O-ring 44 into annular groove 48 provides tactile sensation of the proper positioning of attachment housing 16 with respect to motor housing 12, it will be appreciated that the attachment housing 16 is not positively locked to motor housing 12.

Rather, the configuration of internal cavity 63 closely matches the external configuration of distal portion 51 to create an interference fit sufficient to prevent accidental dislodging of attachment housing 16 from motor housing 12. However, it will be understood that manual pulling along the longitudal axis of attachment housing 16 will easily dislodge the attachment housing from motor housing 12. In this preferred aspect, it is contemplated that the user will not have to operate any mechanical locking members to lock or unlock the attachment housing to the motor housing thereby easing the operation for the end user.

In addition to the ease of coupling the attachment housing 16 to the motor housing 12, it is preferred that the exterior contour of the attachment housing be contoured to provide optimum field of view of the dissection tool 18 dissection head 20 while at the same time providing support of tool shaft 19. More specifically, attachment housing 16 includes a first cylindrical portion 25 having an external diameter slightly less than the external diameter of motor housing 12. First cylindrical portion 25 transitions through first taper 26 to a second smaller diameter cylindrical portion 28. The reduction in diameter continues through tapered section 30 and into third cylindrical portion 32 having still a smaller diameter than cylindrical portion 28. Finally, attachment housing 16 terminates in tapered portion 34.

It will be understood that there is a maximum line of sight 35 through which an end user may still visualize dissection head 20. The transition points 27, 29 and 33 between the cylindrical portions and the small diameter tapering sections provide the first points of obstruction of line of sight 35. As best seen in FIG. 3, line of sight 35 intersects high point 27 and high point 33. In a preferred aspect of the present invention, it is contemplated that maximum line of sight 35 will substantially intersect at least two high points. Still further, it is contemplated that second cylindrical portion have a diameter substantially less than the line of sight to permit engagement with an operator's fingers without undue interference with a maximum line of sight. Still further, the transitions adjacent high points 27, 29 and 33 are radiussed to remove an abrupt corner thereby lowering the height of each high point and increasing the maximum line of sight.

Referring to FIGS. 2B and 3, attachment housing 16 is provided with an internal bore 17 adapted to receive a portion of dissection tool 18. More specifically, internal bore 17 includes a plurality of bearings adapted to rotationally support tool shaft 19. The tool shaft is supported by distal bearing 36 and intermediate bearing 38 and proximal bearing 40. In the preferred embodiment illustrated in FIG. 3, distance D1 represents the distance between the distal bearing 36 and dissection head 20. It will be understood that this distance may vary depending on many variables such as the length and diameter of the cutting tool head, diameter of the tool shaft, etc. Distal bearing 36 is located in the distal most portion of cylindrical portion 32. It will be understood that the angle created by line of sight 35 and the longitudinal axis of dissection tool 18 is shown by angle A1. In the preferred embodiment illustrated in FIG. 3, this angle is approximately 10°. However, it is contemplated that this angle A1 will vary from attachment to attachment and is dependent on tube length and attachment diameter. Still another preferred aspect of the present invention, tapered surface 34 on the leading tip of attachment housing 16 provides a smooth surface over which tissue and other obstructions may readily move. It will be understood that as the device is utilized for the dissection of bone and other tissue, thereto is a desire to minimize snagging on tissue or engaging other obstructions as the dissection tool assembly 10 is utilized in the patient.

Furthermore, disposed internally of distal taper 34, is an internal taper of internal bore 17 transitioning from a large diameter at the distal-most end of internal bore to a smaller diameter approaching the bearing assembly area. Internal taper 37 is provided to permit some minimal flail of tool shaft 19 during operation while still rotationally supporting the shaft. It will be understood that spacing dissection head 20 from distal bearing 36 may induce some flail or angular deflection along the longitudinal axis of tool shaft 19 during operation.

Referring to FIG. 3, there is shown a pneumatically operated motor 80 associated with the dissection tool assembly 10 of the present invention. Motor 80 receives high pressure air from inlet hose 82. High pressure air flows through outlets 84 and impacts vanes 86 to urge rotation towards air outlets 88. The air then exits through low pressure exhaust passage 90. It will be understood that the rotation of vanes 86 drives rotor shaft 92. Although a pneumatic motor is shown for the purpose of illustration, it will be understood that motors using electricity or other motive forces may be utilized with the present invention.

Referring now to FIGS. 3 through 5B, there is shown in detail a coupling assembly 102 in accordance with one aspect of the present invention. Referring more specifically to the exploded perspective view of FIG. 4, coupling assembly 102 includes a collet housing 104 having a helical slot 105 adapted to receive ball bearings 106, and a pair of apertures 107 adapted to receive alignment balls 108. Coupling assembly 102 further includes a housing spacer 110 and an O-ring 112 associated with posterior Double D-collet 114. Posterior Double D-collet 114 is spaced from anterior Double D-collet 118 by shim 116. The assembly further includes O-rings 120 and 122 and tapered nose 124. A number of the remaining components are disposed within collet housing 104. More specifically, spring 126 and ball carrier 128, along with additional components washer 130, seal 132, wave spring 134, bearing tube 136, sleeve keeper 138 and O-ring 140 are assembled within collet housing 104. Coupling assembly 102 also includes hex closure sleeve 142, spring 144, rotor shaft 146, and ball bearings 148 retained in openings 147 in the rotor shaft by retaining ring 150. This internal assembly is completed by bearing 152 and lock ring 154. Coupling assembly 102 is shown in cross-section in its assembled configuration in FIGS. 5A and 5B.

With reference to FIG. 3, it will be understood that proximal portion 156 is received within an internal portion of motor housing exterior cover 81 and firmly affixed thereto by any known attachment mechanism. Rotor shaft 146 engages a portion of rotor shaft 92 of motor 80 to provide a power coupling there between. Rotor shaft 146 includes an internal socket 160 adapted to receive the proximal portion of dissection tool 18. Internal socket includes an alignment pin 162 surrounded by socket end wall 164. Axially disposed adjacent the distal end of alignment pin 162 is an internal shoulder 166. Although the preferred embodiment illustrated in FIG. 3 shows alignment pin 162 as being integral with rotor shaft 146, it is contemplated that these elements may be separate components coupled to each other during the assembly process.

Figure 6A:
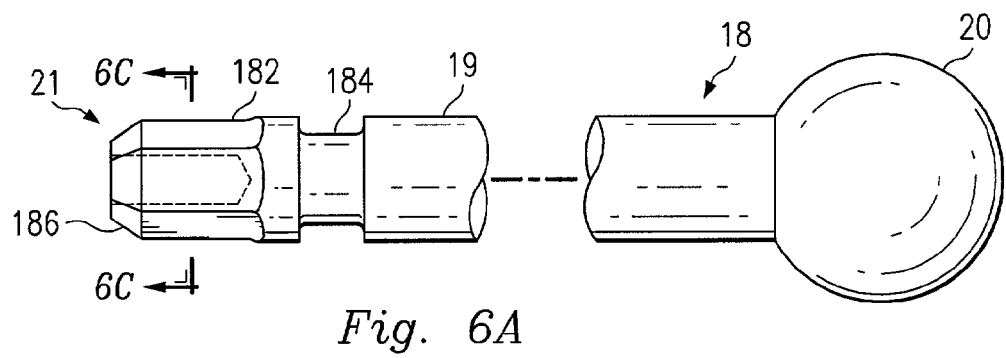
FIG. 6A is a side view of a dissection tool according to another aspect of the present invention.
Figure 6B:
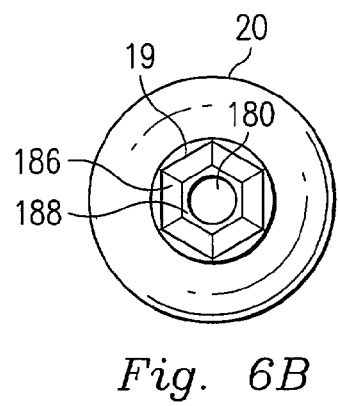
FIG. 6B is an end view of the dissection tool of FIG. 6A.
Figure 6C:
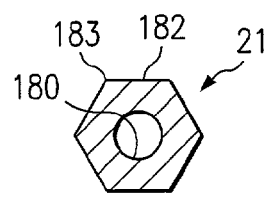
FIG. 6C is a cross-section taken along line 6C—6C in FIG. 6A.
Figure 7A:
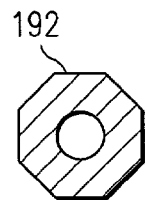
FIG. 7A is a cross-section of an alternative drive area of a dissection tool according to another aspect of the present invention.
Figure 7B:
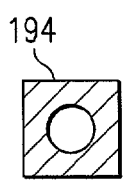
FIG. 7B is a cross-section of an alternative drive area of a dissection tool according to another aspect of the present invention.
Figure 7C:
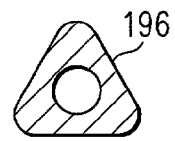
FIG. 7C is a cross-section of an alternative drive area of a dissection tool according to another aspect of the present invention.

Referring now to FIGS. 6A–6C, there is shown a dissection tool in accordance with the present invention. Dissection tool 18 includes an elongated shaft 19, a dissection head 20 and a connection end 21. Connection end 21 includes a plurality of driving surfaces 182. In the preferred embodiment shown in FIG. 6A, driving surfaces 182 are substantially planar and extend in substantially parallel alignment with the longitudinal axis of dissection tool 18. As shown in the cross-section of FIG. 6C, driving surfaces 182 are formed in a substantially hexagonal pattern to define driving corners 183 between each driving surface. Alternative cross-sections of dissection tool 18 adjacent connection end 21 may include eight driving surfaces 192, four driving surfaces 194 or three driving surfaces 196 to form the octagonal, square, or triangular cross-sectional configurations shown in FIGS. 7A, 7B and 7C, respectively. Connection end 21 further includes an alignment bore 180 centered on and extending at least partially along longitudal axis of dissection tool 18. In a preferred aspect, the distal end of alignment bore 180 is in substantial alignment with the distal portion of driving surfaces 182. Adjacent to proximal end of connection end 21 are tapered surfaces 186 transitioning between flat end 188 and drive surfaces 182.

Referring to FIG. 5A, coupling 102 is shown in the unlocked position. Ball 106 is positioned in helical groove 105 in the proximal position. Ball 106 rides in ball carrier 128 and is moved by ball 106 to the proximal position shown in FIG. 5A. In the proximal position, ball carrier 128 urges closure sleeve 142 to compress spring 126 and permits spring 144 to expand to a relaxed position. In the unlocked proximal position, closure sleeve 142 is moved away from locking ball 148 permitting it to move at least partially out of hole 147. However, o-ring 140 tends to urge locking ball 148 into hole 147. This arrangement provides positive positioning of locking ball 148 in hole 147 and into channel 158 such that upon insertion of coupling end 21 into socket 160, locking ball 148 will snap into annular groove 184 providing tactile feedback to the user that coupling end 21 is properly positioned in coupling assembly 102.

Figure 6D:
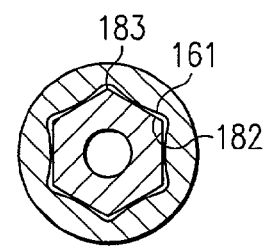
FIG. 6D is the cross-sectional view of FIG. 6C illustrating the driving socket.

Dissection tool 18 is advanced within channel 158 until coupling end 21 is disposed adjacent alignment pin 162. Co-axial with alignment pin 162, socket 160 has a plurality of drive surfaces 161. In the preferred embodiment shown, drive socket 160 has six drive surfaces 161 arranged in a hexagonal pattern substantially matching the hexagonal pattern of FIG. 6A. However, in a preferred aspect of the invention shown in FIG. 6D, drive surfaces 161 are convexly shaped such that they tend to engage a central portion of surface 182 spaced from corner 183. In some applications, rotation speeds are approximately 70,000 rpm such that good connection between surfaces 161 and surface 182 is necessary. As dissection tool 18 is advanced, tapered surfaces 186 may engage internal shoulder 166 at the beginning of the drive surfaces 161 to establish initial axial alignment. In a preferred aspect, such engagement between tapered surfaces 186 and internal shoulder 166 also tends to rotationally align planar driving surfaces 182 with planar driving surfaces 161. It is contemplated that this feature may be a straight chamfer as opposed to the hex chamfer shown in FIG. 6A. Thus, tool coupling end 21 includes a mechanism for rotational alignment. As the tool is further advanced into socket 160, tapered tip 163 on alignment pin 162 may enter alignment bore 180 and engage a portion of the alignment bore to adjust the longitudinal axis of tool shaft 19 into substantial alignment with the longitudinal axis of rotor shaft 146. In a preferred aspect there is a close tolerance between the internal diameter of the alignment bore 180 and the external diameter of the alignment pin 162 such that as the pin advances in the bore there is substantial parallel alignment between the cylindrical surfaces of the pin and bore, with the resulting substantial axial alignment between the longitudinal axis of the tool shaft 19 and longitudinal axis of the rotor shaft 146.

After dissection tool coupling end 21 has been properly positioned in coupling assembly 102, proximal Double D collet 114 may be rotated with respect to the other elements of the housing to urge ball 106 and ball carrier 128 to their distal, locking position shown in FIG. 5B. FIG. 5B shows a cross-section of coupling assembly 102 with proximal Double D collet 114 and balls 106 shown in the position of FIG. 5A and the remaining elements rotated approximately 90° with respect to the orientation shown in FIG. 5A. It will be understood that in operation of the illustrated preferred embodiment, proximal Double D collet 114 and balls 106 are moved while the other element remain stationary. As ball carrier 128 advances distally, spring 140 is compressed and spring 126 is allowed to expand. As spring 126 expands, it urges closure sleeve 142 distally. Internal taper surface 143 of closure sleeve 142 engages locking ball 148 and urges it into locking engagement with annular groove 184. Closure sleeve 142 continues to advance over locking ball 148 to securely hold locking ball 148 in the annular groove 184, thereby inhibiting movement of dissection tool 18 along the longitudinal axis. In the preferred embodiment illustrated, annular groove 184 is uniformly concave in longitudinal cross-section and does not actively participate in the transmission of rotational force to tool shaft 19. However, it is contemplated that annular groove may include surface configurations adapted to receive rotational force and may thereby cooperate in driving tool shaft 19.

As previously described, attachment housing 16 includes an internal cavity 63 having a configuration substantially matching the external configuration of coupling assembly 102. More specifically, in a preferred aspect the proximal portion of internal cavity 63 includes driving flat 64 (FIG. 3) substantially matching flat 56 and opposing flat (not shown) and internal cylindrical portions (not shown) substantially matching cylindrical portion 58 and the opposing cylindrical portion (not shown) on the coupling assembly. Similarly, internal cavity 63 includes an internal cylindrical portion 66 disposed adjacent flat 52 and cylindrical portion 54. Thus, as the attachment housing 16 is advanced over distal portion 51, driving flat 64 initially aligns with and guides over flat 52. When positioned in the operation position shown in FIG. 3, driving flat 64 is positioned over flat 56 and does not extend to flat 52. In use, as the attachment housing 16 is rotated with respect to motor housing 12, driving flat 64 cooperates with flat 56 to rotate proximal Double D collet 114 to the locked position while internal cylindrical portion 66 rotates over flat 52. It will be understood that as flat 64 rotates past cylindrical portion 54, attachment housing 16 becomes locked to motor housing 12. As shown in FIG. 3, proximal shoulder 60 of cylindrical portion 54 engages distal shoulder 62 of driving flat 64. It will be understood that the single partial rotation of the attachment housing 16 about the longitudinal axis of motor housing 12 positively locks both dissection tool 18 to coupling assembly 102 and attachment housing 16 to motor housing 12.

Referring now to FIGS. 8A through 8D, a further embodiment of a coupling assembly and dissection tool according to the present invention are illustrated. Coupling assembly 202 has a number of attributes in common with the embodiment shown in FIGS. 3 through 5B and may cooperate with the assembly housing 16 and motor housing 12 in the manner previously described. Coupling assembly 202 includes collet housing 204 having slot 205 and holes 207. Ball bearings 206 and alignment balls 208 are configured to at least partially engage slot 205 and holes 207, respectively. As with the earlier described embodiment, Double D sleeve 214 is provided to engage attachment housing 16 and move the coupling assembly between the unlocked and locked positions.

Coupling assembly 202 includes a number of components internally positioned within collet housing 204. Such internal components include spring 244, anterior spring shim 247, ball carrier 248, closure sleeve 230 and spring 226. Disposed within closure sleeve 230 is the rotor shaft 260 with a non-integral alignment pin 262. A pair of bearings 250 and 252 are provided to support rotor shaft 260.

Referring now to FIG. 8B, tool shaft 296, rotor shaft 260 and alignment pin 262 are shown in partial cross-sectional perspective view. Tool shaft 296 is shown having a coupling end with an alignment channel 297 extending along and in substantial alignment with the longitudinal axis L2 of the tool shaft. The coupling end also includes annular groove 298 and annular shoulder 299. Rotor shaft 260 includes four flexible gripping fingers 265 spaced from each other by openings 268 and integral with uninterrupted cylindrical portion 273. Rotor shaft 260 includes an internal bore 261 adapted to receive alignment pin 262 with projection 264. Alignment pin 262 may be joined to rotor shaft 260 via a mechanical pin connection transverse to the longitudinal axis or by any other suitable connection. Each gripping finger 265 includes an internal leading taper surface 267 adjacent the distal end. Drive surface 266 is disposed adjacent to taper surface 267 followed by annular internal groove 269 on each gripping finger 265. The exterior of each gripping finger 265 includes annular ridge 270, external annular recess 272, taper section 274 and second ridge 276.

Figure 8C:
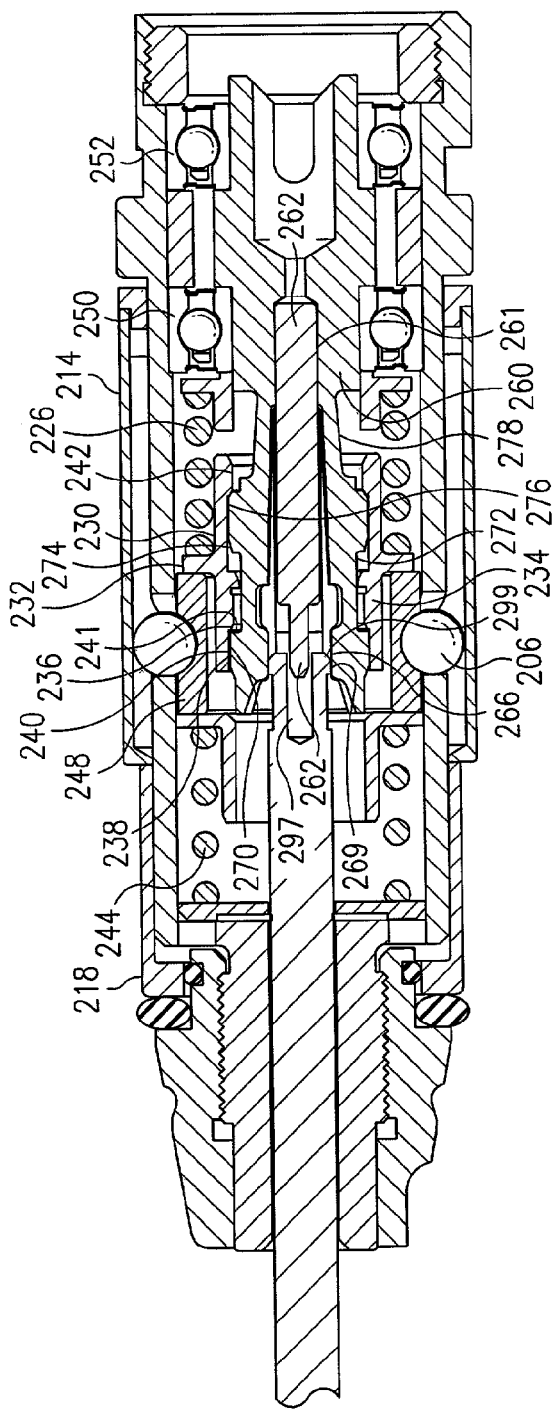
FIG. 8C is a partial cross-sectional side view of the assembled apparatus of FIG. 8A in the unlocked position.

Referring to FIG. 8C, the coupling assembly 202 is shown in the open position. Spring 226 is compressed by proximal movement of closure sleeve 230 resulting from the movement of ball carrier 248 against rib 232. With the closure sleeve 230 in the proximal position, distal spring 244 is in an expanded condition. Closure sleeve 230 includes internal annular rings 240 and 242. In the open position, annular rings 240 and 242 are positioned over annular recess 272 and reduced diameter portion 278, respectively, of the rotor shaft. In the unlocked position, fingers 265 are free to splay to permit passage of the enlarged projecting shoulder 299 of tool shaft 296. Internal surface 238 on closure sleeve 230 limits the amount of splay of fingers 265. Reduced diameter portion 278 provides an area of strain relief and flexibility to permit the outward movement of fingers 265. As previously described, alignment projection 262 cooperates with alignment channel 297 on tool shaft 296 to provide axial alignment of the tool shaft and the rotor shaft along longitudinal axis L2.

Figure 8D:
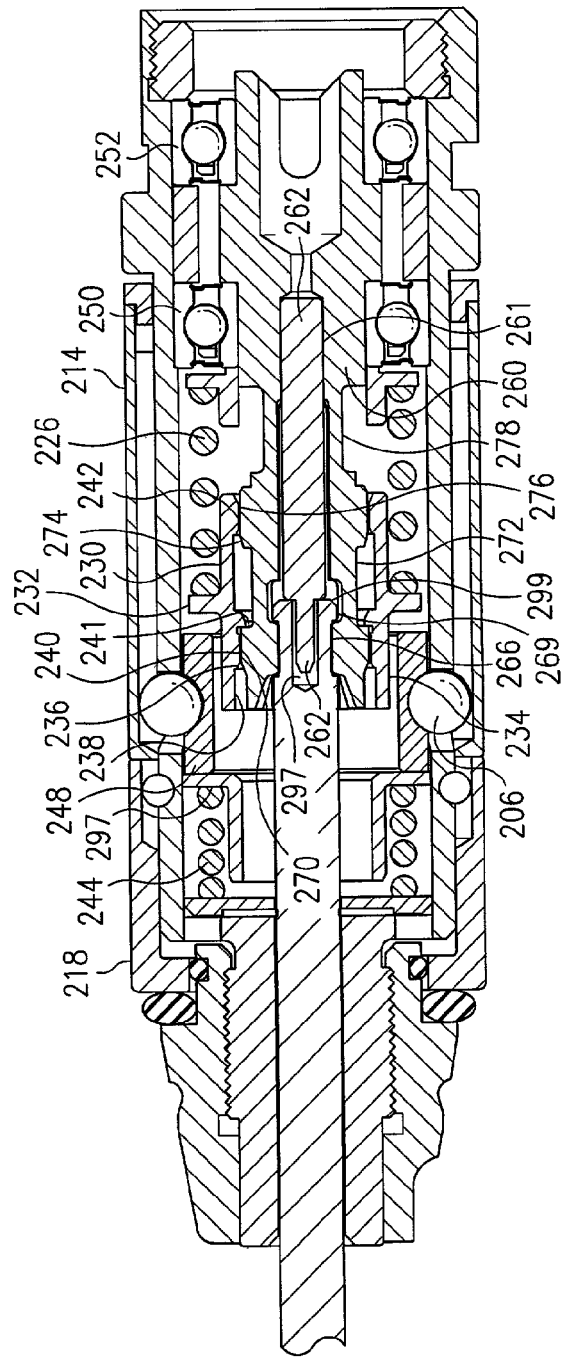
FIG. 8D is a partial cross-sectional side view of the assembled apparatus of FIG. 8A in the locked position.

Referring to FIG. 8D, coupling assembly 202 is shown in the locked position around tool shaft 296. As previously described, in a preferred embodiment the attachment assembly 16 is rotated to move Double D collet 214 and drive ball 206 along slot 205. This movement moves ball carrier 248 distally to compress spring 244. Spring 226 then acts on rib 232 to move closure sleeve 230 distally over rotor shaft 260. As closure sleeve 230 advances distally, taper surface 236 engages shoulder 241 of ridge 270 while taper surface 274 engages ridge 276, each acting to close driving surfaces 266 on annular groove 298. Once the locking diameter of rotor shaft is achieved, closure sleeve 230 continues distally to bring internal annular rings 240 and 242 into engagement with ridges 270 and 276 to thereby lock rotor shaft 260 in the locking position. Engagement of groove 269 and shoulder 299 prevent withdrawal of the tool shaft from the coupling assembly. It will be understood that alignment projection 264 maintains longitudinal alignment of the tool shaft during the closing of the locking fingers thereby assuring that proper axial alignment is achieved when the coupling assembly is locked.

Referring now to FIGS. 9A and 9B, a coupling assembly 302 according to another aspect of the present invention is shown. As with previously described preferred embodiments, coupling assembly 302 utilizes a ball 310 and ball carrier 308 in a spring biased relationship between springs 304 and 306 to move the coupling closure sleeve 312 between the unlocked and locked positions. While the foregoing has been shown in the preferred embodiments, such is provided for the purpose of illustration it being understood that alternative mechanisms for controlling the coupling assembly between the locked and unlocked positions is contemplated. Rotor shaft 315 includes an internal bore adapted to receive alignment shaft 330 with projecting alignment pin 332. In the present embodiment, alignment shaft 330 includes a transverse bore 334 and a pin 336 extending from rotor shaft 315 into the bore to join the alignment shaft and rotor shaft. Rotor shaft 315 includes a plurality of apertures 316 adjacent the distal end. A plurality of grippers 350 are attached to rotor shaft 315. Each gripper includes a driving face 352 extending through aperture 316 and selectively into channel 320. Distal end 322 of rotor shaft includes an external flange and a plurality of detents 324 in the flange. The detents receive a portion of each gripper 350. Further, the bottom of each detent includes a rounded projection 324. Each gripper 350 includes a concave detent 354 riding over rounded projection 318. It will be understood that grippers 350 may pivot about the engagement between projection 318 and detent 354. Grippers 350 also include an enlarged end 356 opposite driving face 352. Tension band 360, such as an o-ring or spiral band, is disposed proximally of the pivot point at detent 354 to bias driving face 352 to extend through aperture 316 an into channel 320. It will be understood that the bias force of o-ring 360 may be relatively easily overcome, with closure sleeve 312 moved proximally into the unlocked position (not shown), by inserting a tool shaft and that driving face 352 will snap against the corresponding driving surface on the tool shaft to provide a tactile feedback to the user that the tool shaft is properly positioned in the coupling assembly.

In use, a tool shaft coupling end is inserted into channel 320 until it is seated in the coupling assembly with alignment pin 332 providing proper longitudinal alignment. Closure sleeve 312 may then be advanced distally such that internal taper 314 acts against grippers 350. As rotational force is applied to rotor shaft 315 the centrifugal force acting on enlarged end 356 will be transmitted by pivot about projection 324 to increase the compressive force of driving faces 352 against the tool shaft. As the rotational speed of rotor shaft 315 is increased, the compressive force of driving faces 352 against the tool shaft will have a corresponding increase.

Figure 10A:
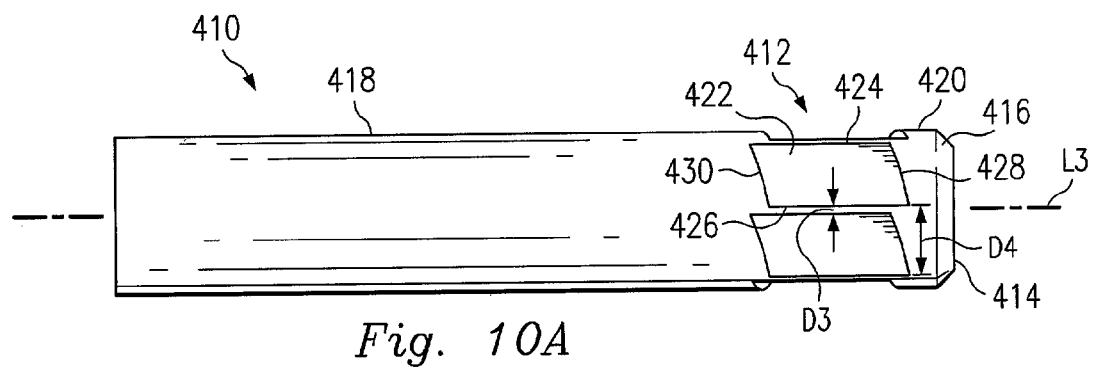
FIG. 10A is a side view of an alternative drive area of a dissection tool according to another aspect of the present invention.
Figure 10B:
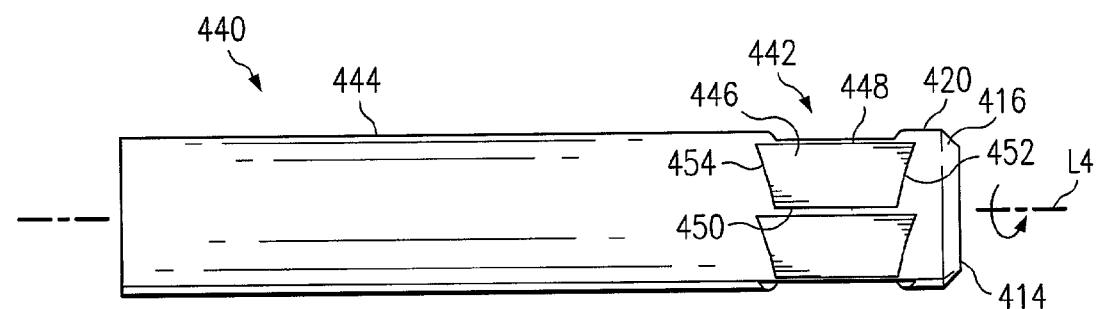
FIG. 10B is a side view of alternative drive area of a dissection tool according to another aspect of the present invention.
Figure 10C:
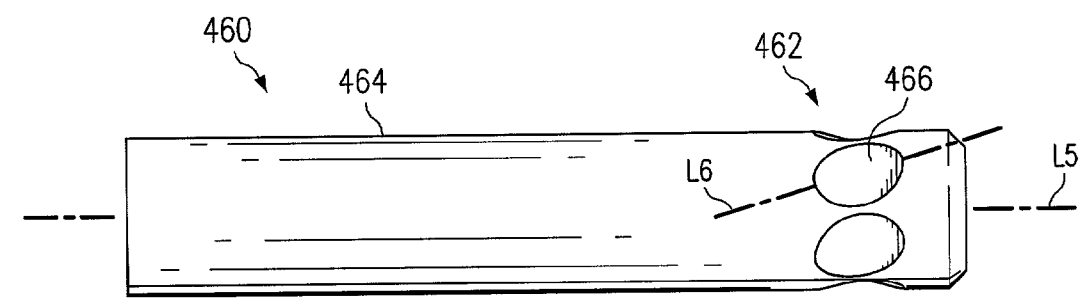
FIG. 10C is a side view of alternative drive area of a dissection tool according to another aspect of the present invention.

Referring to FIGS. 10A through 10C, a series of tool shaft coupling configurations are shown. Dissection tool shaft 410 has a coupling configuration 412 adapted to be engaged by driving members of a coupling assembly. Dissection tool 410 has a proximal end 414, adjacent taper surface 416 extending to cylindrical portion 420. A plurality of drive surfaces 422 are formed adjacent the proximal end. In the embodiment shown in FIG. 10A, there are six planar drive surfaces 422. Each drive surface 422 includes corners 424 and 426 extending substantially parallel to longitudinal axis L3. Further, each drive surface 422 includes a pair non-orthogonal drive shoulders 428 and 430 extending substantially parallel to each other and at a non-orthogonal angle with respect to longitudinal axis L3. It will be appreciated that driving members in many applications often strip or round driving corners such that torque can no longer be transmitted. As shown in FIG. 10A, the distance D3 between adjacent drive faces represents the amount of material that would need to be deformed or removed to permit a driving member to jump to the next drive surface. In contrast, with the non-orthogonal drive shoulders 428 and 430, material along the distance D4, approximately ⅙ of the circumference of cylindrical portion 420, would have to be deformed or removed to permit a driving member to jump to the next drive surface. In other words, the driving surface configuration includes a structures to inhibit stripping or jumping along the entire transverse width of the driving surface. Additionally, the driving member will at least partially drive against shoulder 428 generating both a rotational force vector and a longitudinal force vector tending to force dissection tool 410 into the collet assembly. It will be appreciated that a surface 422 configured as illustrated accomplishes both a driving function and a holding function when used in a mating collet assembly.

Referring to FIG. 10B, a dissection tool 440 with drive end 442 and cylindrical body 444 is shown. Drive end 442 includes a plurality of drive surfaces 446 extending around the circumference and within the diameter of cylindrical body 444. Each drive surface 446 includes drive corners 448 and 450 extending substantially parallel to longitudinal axis L4. Further, each drive surface 446 includes a pair of opposed non-orthogonal drive shoulders 428 and 430 extending substantially non-parallel to each other and at a non-orthogonal angle with respect to longitudinal axis L4. As with the previously described embodiment, the driving surfaces 446 increase resistance to stripping and increase the driving surface area for mating with a corresponding driving member. Further, when the driving member (not shown) drives against shoulder 452 it tends to hold the tool in the collet.

FIG. 10C shows still a further embodiment of a dissection tool 460 having non-orthogonally oriented driving surfaces. Driving surface 466 is a non-planar, substantially elliptical surface adapted to receive a portion of a spherical driving member. Driving surface 466 is formed by impinging upon the cylindrical surface 464 with a ball end mill (not shown) oriented at non-perpendicular angle with respect to longitudinal axis L5. In a preferred embodiment the angle of incidence of the ball end mill is about 15° with respect to the transverse axis of dissection tool 460. As previously described with respect to the embodiments of FIGS. 10A and 10B, spherical driving members disposed in the elliptical surfaces 466 may tend to apply force or travel at least partially along the axis L6 rather than purely transverse to the longitudinal axis L6 to thereby increase the driving surface area and hold the tool in the collet assembly.

Referring to FIGS. 11A–11D, a surgical instrument for the dissection of bone and other tissue constructed in accordance with the teachings of another preferred embodiment of the present invention is illustrated and generally identified at reference numeral 1010. The surgical instrument 1010 is illustrated to generally include a dissection tool 1012 and a quick release coupling arrangement 1014 for engaging the dissection tool 1012. The teachings of the illustrated preferred embodiment of the present invention are primarily directed to features of the dissection tool 1012 and the quick release coupling arrangement 1014 which cooperate to center and retain the dissection tool 1012 with respect to the surgical instrument 1010. Additional features of the surgical instrument 1010 are described in U.S. Pat. No. 5,505,737 which is hereby incorporated by reference.

Figure 11A:
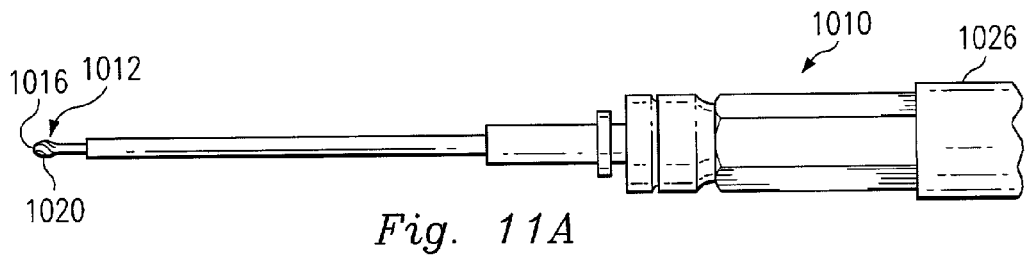
FIG. 11A is a side elevational view of a surgical instrument for the dissection of bone and other tissue according to the teachings of another embodiment of the present invention.

The dissection tool 1012 of the surgical instrument 1010 includes a substantially cylindrical shaft having a distal end 1016 and a proximal end 1018. The distal end 1016 of the dissection tool 1012 includes a cutting element 1020, while the proximal end 1018 defines a centrally located cylindrical bore 1022. As illustrated, the bore 1022 distally extends only partially along a central axis 1024 of the dissection tool 1012. Alternatively, the bore 1022 may distally extend substantially along the central axis 1024. The length of the bore 1022 is limited only by applications utilizing a closed end cutting element 1020, as illustrated in FIG. 11A. In a manner to be discussed below, the bore 1022 cooperates with a centrally located pin 1021 in the spindle of the surgical instrument 1010 so as to center the dissection tool 1012 within the surgical instrument 1010 along the longitudinal axis. In a preferred aspect, pin 1021 is substantially co-axial and co-terminus with locking member 1040. It will be understood that the coupling mechanism also prevents the insertion of a dissection tool not design for use with the surgical tool 1010 from being operatively engaged with the surgical tool 1010.

In the embodiment illustrated in FIGS. 11A–11D, the dissection tool 1012 further includes a cap 1026 formed of a first material which is secured to the remainder of the dissection tool 1012. In one particular application, the cap 1026 is formed of stainless steel, such as 440 stainless steel, and the remainder 1029 of the dissection tool 1012 is formed of tool steel. In certain applications, it may be desirable to injection mold the cap 1026 from plastic.

Such a dual material construction of the dissection tool 1012 permits the distal end 1016 of the dissection tool 1012 to be made of a harder material to facilitate the cutting action of the dissection tool 1012, while the proximal end 1018 can be constructed of a softer material that is easier to machine so as to form the bore 1022. The cap 1026 defines a generally cylindrical female opening 1028 which receives a male extension 1030 of the dissection tool 1012. Those skilled in the art will readily appreciate that materials other than that specifically identified can be incorporated. Alternatively, the dissection tool 1012 can be unitarily constructed of a single material. Further, cap 1026 may be removably coupled to dissection tool 1012. In this type of embodiment, cap 1026 may act as an adaptor to permit suitable tools having alternative proximal configurations to be used in the coupling.

The surgical instrument 1010 is illustrated to further include a spindle 1034 which engages and drives the dissection tool 1012 about the axis of the spindle 1034, and is driven by a motor portion 1035 of the surgical instrument 1010. The distal end of the spindle 1034 defines a cylindrical cavity 1036 for receiving the proximal end 1018 of the dissection tool 1012. While in the embodiment illustrated, the spindle 1034 is illustrated as a unitary member, a separate attachment member (not shown) may be used to define the cavity 1036 for receiving the dissection tool 1012 which in turn is secured to the spindle 1034.

Figure 11B:
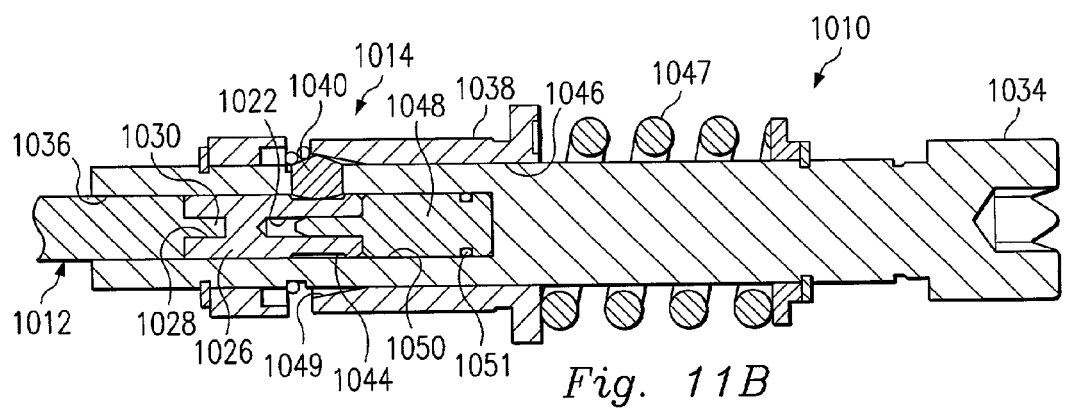
FIG. 11B is a cross-sectional view of a portion of the surgical instrument for the dissection of bone and other tissue according to the teachings of FIG. 11A.
Figure 11C:
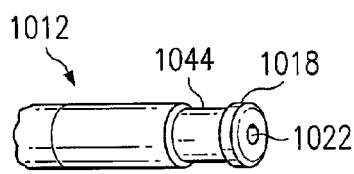
FIG. 11C is a perspective view of a proximal end of a dissection tool used with the surgical instrument for the dissection of bone and other tissue according to the teachings of FIG. 11B.
Figure 11D:
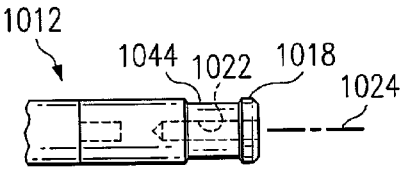
FIG. 11D is a side view of the dissection tool used with the surgical instrument for the dissection of bone and other tissue according to the teachings of FIG. 11B.

The quick release coupling arrangement 1014 of the surgical instrument 1010 is generally illustrated to include a sleeve 1038 and grippers or locking members 1040. In the embodiment illustrated, the surgical instrument 1010 is shown to include a three locking members 1040. The shape of each locking member 1040 is generally in the form of a cylindrical section having a convexly shaped cross-sectional exterior surface and a generally flat cross-sectional inner surface. The inner surface of the locking member 1040 is operable to engage a reduced diameter portion 1044, while the outer surface of the locking member 1040 is able to engage the sleeve 1038. Each of the locking members 1040 are disposed within a radially extending aperture 1042 formed in the spindle 1034 and intersecting the cavity 1036. The locking members 1040 are positioned and sized to be received within a reduced diameter portion 1044 of the dissection tool 1012 when the dissection tool 1012 is fully inserted into the cavity 1036 as shown in FIG. 11A and FIG. 11B.

The sleeve 1038 is generally tubular in shape and includes a central aperture 1046 for receiving the spindle 1034. The sleeve 1038 is movable axially along the spindle 1034 between a first position and a second position. In the first position shown in FIG. 11B, the sleeve 1038 maintains engagement of the locking members 1040 with the reduced diameter portion 1044 of the dissection tool 1012 thereby both preventing (1) inadvertent withdrawal of the dissection tool 1012 from the surgical instrument 1010 and (2) rotatably coupling the dissection tool 1012 with the spindle 1034. In the second position (not shown), the sleeve 1038 is shifted proximally (to the right as shown in FIG. 11B) to allow the locking members 1040 to be displaced radially from the reduced diameter portion 1044 of the dissection tool 1012. In this second position of the sleeve 1038, the dissection tool 1012 maybe withdrawn from the cavity 1036 for quick and easy replacement.

The surgical instrument 1010 further includes a biasing mechanism for normally biasing the sleeve 1038 to its first position. In the embodiment shown, the biasing mechanism includes a coil spring 1047 surrounding a portion of the spindle 1034 which places a distally biasing force on the sleeve 1038. Accordingly, the sleeve 1038 is biased by the coil spring 1047 in such a manner as to cause the locking members 1040 to engage the reduced diameter portion 1044.

To facilitate movement of the sleeve 1038 over the locking members 1040, the sleeve 1038 includes a tapered section 1049. The tapered portion 1049 is located at the distal end of the sleeve 1038 and is oriented so that the inner surface of the sleeve 1038 defined by the tapered portion 1049 has increasing diameter in the region adjacent to the locking members 1040. Accordingly, as the sleeve 1038 moves distally, the tapered portion 1049 is able to slide against the outer surface of the locking members 1040 and progressively force the locking members 1040 against the reduced diameter portion 1044 of the dissection tool 1012.

The surgical instrument 1010 further includes a plug 1048 that extends from the spindle 1034 into the cavity 1036. Plug 1048 includes an axially aligned pin 1021 extending distally and having a reduced diameter. The plug 1048 further includes a shoulder adjacent pin 1021 and extending transverse to the longitudinal axis. When the dissection tool 1012 is fully inserted into the cavity 1036, the pin 1021 extends into the bore 1022 of the dissection tool 1012 thereby ensuring proper alignment of the axis 1024 of the dissection tool 1012 with a rotation axis of the spindle 1034. Additionally, proximal end 1018 may abuttingly engage the shoulder to ensure that reduced diameter portion 1044 is aligned with locking members 1040. The pin 1048 is secured to the spindle 1034 within an aperture 1050 defined in the rotary driveshaft 1034 through an interference fit. To improve the tactile feel received by the user of the surgical instrument 1010 during the installation of the dissection tool 1012 into the spindle 1034, a split spring ring or O-ring 1051 may be incorporated as shown in FIG. 11B. The tactile component 1051 maintains the locking members 1040 in a seated, but movable position. The combined spring action of the locking members 1040 and the tactile component 1051 provide feedback to the user when the flange on the dissection tool 1052 passes the locking members 1040.

Figure 12:
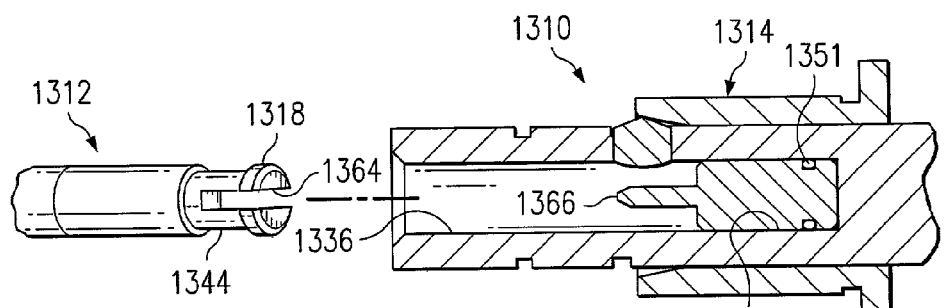
FIG. 12 is a partial cross-sectional view of a portion of the surgical instrument for the dissection of bone and other tissue according to the teachings of another embodiment of the present invention.

With reference to FIG. 12, a surgical instrument 1310 for the dissection of bone and other tissue according to be teachings of another preferred embodiment of the present invention is illustrated. The surgical instrument 1310 according to the fourth preferred embodiment of the present invention is similar to the surgical instrument 1010. In this regard, a dissection tool 1312 is able to be secured by a quick release coupling arrangement 1314 by inserting the proximal end 1318 of the dissection tool into the cavity 1336. The dissection tool 1312 further includes a slot 1364, having planar side walls, which extends proximally into the dissection tool 1312 approximately same distance has the pin 1048 of the surgical instrument 1010 shown in FIG. 1B. The slot 1364 is able to receive an insert 1366 which is located at the proximal end of the cavity 1336. An O-ring 1351 is incorporated between the insert 1366 and the cylindrical aperture 1350. It will be appreciated that slot 1364 may cooperate with insert 1366 to transmit torque from the motor to dissection tool 1312.

Turning to FIGS. 13A–13C, a surgical instrument 1410 for the dissection of bone and other tissue according to the teachings of another preferred embodiment of the present invention is illustrated. The surgical instrument 1410 according to another preferred embodiment of the present invention shares various common elements with the surgical instrument 1010 of a preferred embodiment of the present invention. For this reason, like reference numerals are used to identify substantially identical elements. The surgical instrument 1410 differs from the surgical instrument 1010 in that a dissection tool 1412 of the surgical instrument 1410 is able to be intra-operatively telescoped between a retracted position (as shown in FIG. 13B) and a fully extended position (as shown in FIG. 13C).

The proximal end of the dissection tool 1412 is formed to include a plurality of reduced diameter portions 1044. In the embodiment illustrated, the dissection tool 1412 is shown to include five such reduced diameter portions 1044. However, those skilled in the art will readily appreciate that a greater number or a lesser number of reduced diameter portions 1044 may be incorporated within the scope of the present invention.

The proximal end of the dissection tool 1412 further includes a centrally located cylindrical bore 1022 extending co-axially and substantially co-terminus with reduce diameter portions 1044. As with the first preferred embodiment, the bore 1022 cooperates with a pin 1048 that extends from the spindle 1034 into the cavity 1036. The pin 1048 extends into the bore 1022 of the dissection tool 1412 so as to ensure proper alignment of an axis of the dissection tool 1412 with a rotational axis of the spindle 1034.

Each of the reduced diameter portions 1044 is adapted to selectively receive the locking members 1040. In FIG. 13B, the locking members 1040 are shown engaging a distal-most reduced diameter portion 1044. In FIG. 13C, the locking members 1040 are shown engaging a proximal-most reduced diameter portion 1044. The locking members 1040 may similarly engage the intermediate reduced diameter portions 1044. In this manner, a surgeon can intra-operatively telescope the dissection tool 1412 when the sleeve 1038 is retracted against the bias of the coil spring 1047. In the embodiment illustrated, the reduced diameter portions 1044 effectively define five positive positions for telescoping of the dissection tool 1412 relative to the sleeve 1038. In this application, the reduced diameter portions 1044 each have a length of approximately 0.081 inches and lands between adjacent reduced diameter portions 1044 each have a length of approximately 0.068 inches. Further in this particular application, the dissection tool 1412 can telescope approximately 0.5 inches between the fully retracted position and the fully extended position.

With reference to FIG. 14, a dissection tool 1510 in accordance with the teachings of another preferred embodiment of the present invention is illustrated. It will be understood that the dissection tool 1510 is adapted to be used with the surgical tool 1410 of the fifth preferred embodiment of the present invention, for example. The dissection tool 1510 differs from the dissection tool 1412 in that it includes a single, elongated reduced diameter portion 1512. The locking members 1040 can engage the reduced diameter portion 1412 anywhere along its length. In this manner, the dissection tool 1510 can be infinitely adjusted telescopically relative to the sleeve 1038 between a fully retracted position and a fully extended position.

With reference now to FIGS. 15A–15D, a dissection tool 1610 according to the teachings of still another preferred embodiment of the present invention is illustrated. The dissection tool 1610 is intended for use, for example, in the surgical tool 1010 of FIG. 11A. Dissection tool 1610 includes an alignment bore 1618 with a chamfer 1620 disposed adjacent the proximal end. The dissection tool 1610 differs from the dissection tool 1012 in that a reduced diameter portion 1614 is defined by a plurality of facets or sides 1616. In all other respects, it will be understood that the dissection tool 1610 and 1612 are substantially identical.

In the embodiment illustrated, the reduced diameter portion 1016 is illustrated to include nine (9) sides 1616. The sides 1616 are equally spaced about the outer diameter of the reduced diameter portion 1614. The sides 1616 are selectively engaged by the locking members 1040 depending on the orientation of the dissection tool 1610.

It will be understood that the dissection tool 1610 may include a greater or lesser number of sides 1616 within the scope of the present invention. Preferably, the number of sides 1616 is equally divisible by the number of locking members 1040. In the embodiment illustrated, the nine sides 1616 are equally divisible by the three locking members 1040. In this manner, the three locking members 1040, which are equally spaced about the reduced diameter portion 1614, each engage one of the sides 616 of reduced diameter portion 1614.

Figure 15A:
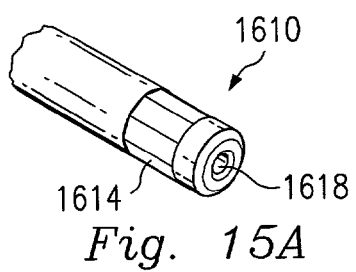
FIG. 15A is a perspective view of a proximal end of a dissection tool of a surgical instrument for the dissection of bone and other tissue according to the teachings of still a further preferred embodiment of the present invention.
Figure 15B:
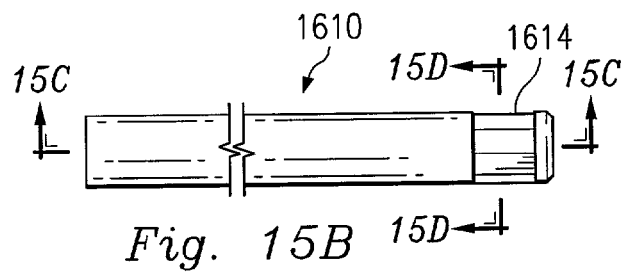
FIG. 15B is a side view of the dissection tool according to the teachings of another preferred embodiment of the present invention.
Figure 15C:
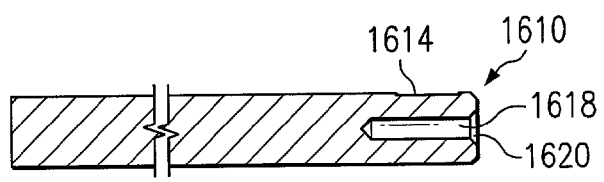
FIG. 15C is a cross-sectional view taken along the line 15C—15C of FIG. 15B.
Figure 15D:
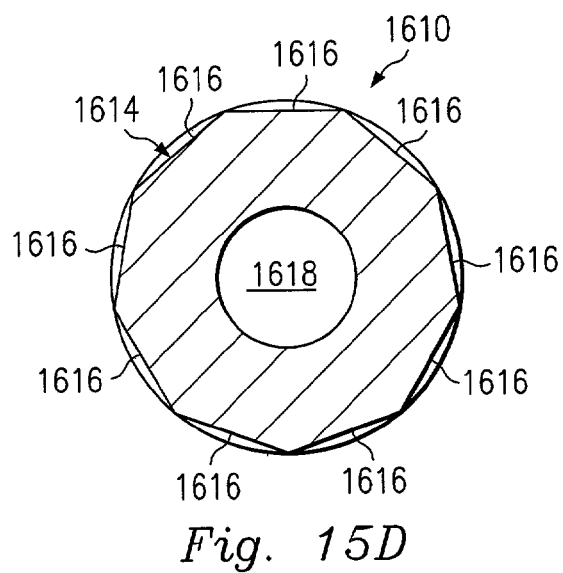
FIG. 15D is a cross-sectional view taken along the line 15D—15D of FIG. 15B.
Figure 16:
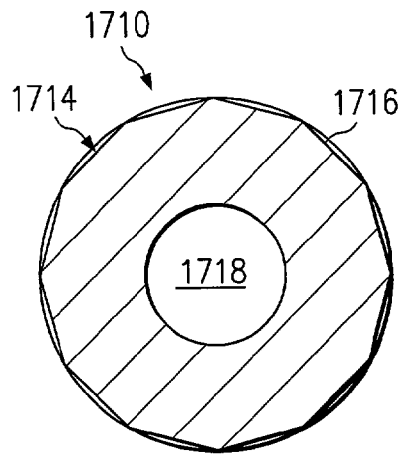
FIG. 16 is a cross-sectional view similar to FIG. 15D illustrating a dissection tool according to the teachings of another preferred embodiment of the present invention.
Figure 17C:
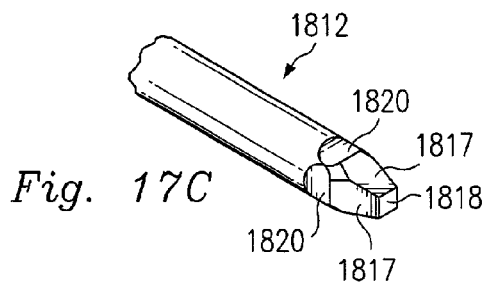
FIG. 17C is a perspective view of the proximal end of a dissection tool of the surgical instrument for the dissection of bone and other tissue according to FIG. 17B.
Figure 17D:
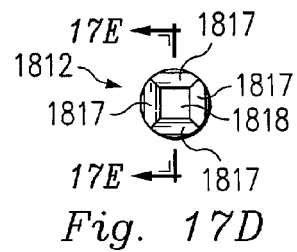
FIG. 17D is an end view of the dissection tool of FIG. 17C.
Figure 17E:
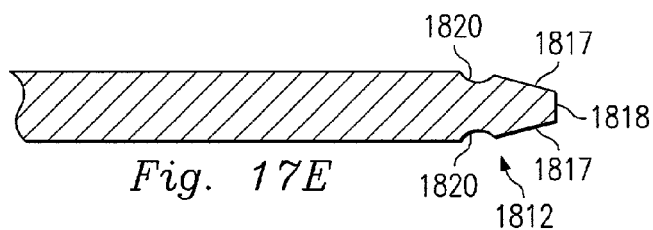
FIG. 17E is a cross-sectional view taken along the line 17E—17E of FIG. 17D.

A cross-sectional view similar to FIG. 15D is shown in FIG. 16 and illustrates a dissection tool 1710 in accordance with an eighth preferred embodiment of the present invention. The dissection tool 1710 includes a reduced diameter portion 1714 having a plurality of sides 1716 and an alignment bore 1718. In this example, the reduced diameter portion is defined by twelve (12) sides 1716. This is but a second example of a reduced diameter portion defined by a plurality of sides which is equally divisible by the number of locking members. Explaining further, if the surgical tool 1010 were constructed to include four (4) locking member 1040 equally spaced about a dissection tool, a reduced diameter portion of the dissection tool may include 4, 8, 12 or a higher multiple of four sides.

Turning finally to FIGS. 17A–17E, a surgical tool 1810 constructed in accordance with the teachings of another preferred embodiment of the present invention is illustrated. The surgical instrument is illustrated to generally include a dissection tool 1812, a housing 1814, and a tube assembly 1816. In the embodiment illustrated, the proximal end of the dissection tool 1812 is shown to include a plurality of facets or sides 1817 which taper toward a surface 1818. The proximal end further includes a plurality of recesses 1820. In one particular application, the dissection tool 1812 has a diameter of approximately 0.046 inches and is particularly suited for minimally invasive surgeries, including but not limited to neurosurgery.

The housing 1814 rotatably supports an input or drive shaft 1822 with at least one bearing 1824. The housing 1814 forwardly extends to define a generally cylindrical recess 1826 for receiving the tube assembly 1816. The input shaft 1822 partially extends into the cylindrical recess 1826 and at its distal end defines a pair of flexure arms 1828. In a manner to be addressed more fully below, the flexure arms 1828 of the input shaft 1822 cooperates to selectively retain the dissection tool 1812.

A coupling arrangement 1830 for selectively securing the dissection tool 1812 to the input shaft 1822 is carried by the distal end of the input shaft 1822. The coupling arrangement 1830 is illustrated to include a closure member 1832 for selectively moving the flexure arms 1828 between an open position for permitting insertion and removal of the dissection tool 1812 in a closed position for securing the dissection tool 1812 to the input shaft 1822. The closure member 1832 is generally cylindrical in shape having a first portion 1833 and a second portion 1834, the inner diameter of the second portion 1834 being greater than the inner diameter of the first portion 1833. The closure member 1832 is linearly movable relative to the input shaft 1822 between a clamped position and an unclamped position. The clamped position is shown in the cross-sectional views of FIGS. 17A and 17B.

The closure member 1832 is normally biased to its clamped position by a coil spring 1838. When the closure member 1832 is in the clamped position, the flexure arms 1828 of the input shaft 1822 are disposed within the smaller diameter portion 1833 and the flexure arms 1828 clampingly engage the proximal end of the dissection tool 1812. When the closure member 1832 is translated against the bias of the spring 1838, in a manner to be discussed below, a portion of the flexure arms 1828 extend into the larger diameter portion 1834 and are thereby permitted to spread apart for permitting removal or insertion of the dissection tool 1812.

The tube assembly 1816 is illustrated to include a first or outer tube member 1840 and a second or inner tube member 1842. The inner tube member 1840 carries a plurality of bearings 1844 for rotatably supporting the dissection tool 1812. In the embodiment illustrated, the plurality of bearings includes three bearings 1844. The outer tube member 1840 is sized to be received within the cylindrical recess 1826 defined by the housing 1814. However, a greater or lesser number of bearings may be employed for alternate applications. Bearing guide members 1846 are disposed on either side of the plurality of bearings 1844 and function to facilitate insertion of the dissection tool 1812.

A bearing 1848 is carried by the outer tube member 1840 and is captured between an inwardly extending radial flange 1850 of the outer tube member 1840 and a proximal end of the inner tube member 1842. The bearing 1848 abuts a guide member 1852 which is press fit into a distal end of the closure member 1832. In response to translation of the tube assembly 1816, the bearing 1848 pushes on the guide member 1852 which in turn translates the closure member 1832 from its clamped position (shown in FIG. 17B) to its unclamped position (not shown) against the bias of the spring 1838.

A lock nut 1854 circumferentially surrounds the distal end of the housing 1814 and functions to secure the housing 1814 to the tube assembly 1816. In this regard, the lock nut 1854 is interconnected to the housing 1018 through a plurality of threads 1856. The lock nut 1854 and the housing 1814 include cooperating tapered surfaces 1858 and 1860, respectively. Through these tapered surfaces 1858 and 1860, tightening of the lock nut 1854 causes the housing 1814 to grip the tube assembly 1816 and thereby arrest relative movement therebetween. Correspondingly, untightening of the lock nut 1854 permits withdrawal and insertion of the tube assembly 1816.

As with the surgical tool 1410, the surgical tool 1810 permits a surgeon to intra-operatively adjust the exposed length of the dissection tool 1812.

Figure 18A:
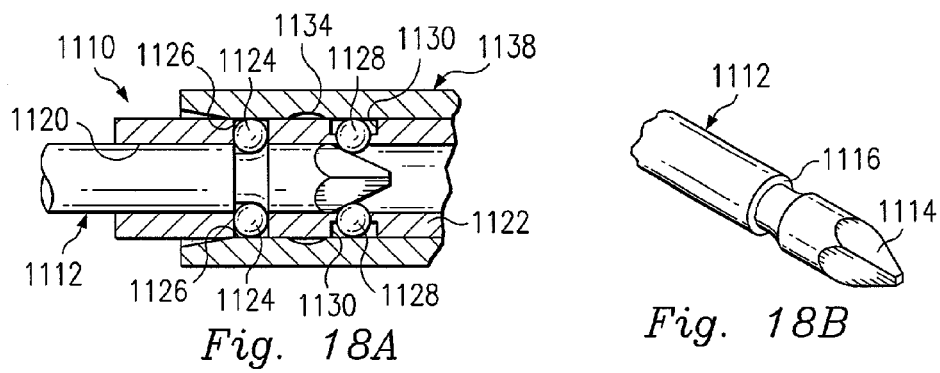
FIG. 18A is a partial cross-sectional side view of still a further dissection tool coupling assembly according to another aspect of the present invention.
Figure 18B:
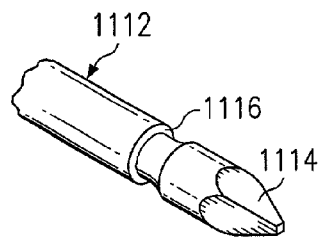
FIG. 18B is a perspective view of the dissection tool of FIG. 18A.

With reference to FIG. 18A or 18B, the surgical instrument for dissection of bone and other tissue in accordance with the teachings of a further preferred embodiment is generally identified at reference numeral 1110. FIG. 18A is a cross-sectional view of a portion of the surgical instrument 1110 similar to the cross-sectional view of FIG. 11B. FIG. 18B is a perspective view of a portion dissection tool 1112.

With the exception of the proximal end of the dissection tool 1112 that is used to secure the dissection tool 1112 to the surgical instrument 1110, it will be understood that the dissection tool 1112 is otherwise substantially identical to the dissection tool 1012. As shown in FIG. 18B, the proximal end of the dissection tool 1112 includes a plurality of facets or sides 1114 which taper toward a point. In the embodiment, the dissection tool 1112 includes four tapered sides 1114. However, those skilled in the art will readily appreciate that any number of tapered sides 1114 may be incorporated within the scope of the present invention. In addition, the dissection tool 1112 further includes a reduced diameter section 1116 which is used to receive a plurality of locking balls 1124 described below.

The dissection tool 1112 is received within a cylindrical aperture 1120 defined the spindle 1122 of the surgical instrument 1110. A first pair of locking balls 1124 are disposed within radially extending apertures 1126 provided in the spindle 1122. The radially extending apertures 1126 intersect the cylindrical cavity 1120 so as to allow the locking balls 1124 to selectively engage the reduced diameter section 1116 of the dissection tool 1112. A pair of drive balls 1128 are similarly located in a corresponding pair of radially extending apertures 1130 defined in the spindle 1122 which intersects the generally cylindrical aperture 1120. Upon full insertion of the dissection tool 1112 into the generally cylindrical cavity 1120, the pair of drive balls 1128 engage two of the tapered sides 1114 of the dissection tool 1112. The drive balls 1128 engage the dissection tool 1112 to rotatably interconnect the spindle 1122 and the dissection tool 1112. In addition, the engagement of tapered sides 1114 and drive balls 1128 function to center the dissection tool 1112 within the generally cylindrical aperture 1120 and in alignment with the longitudinal axis.

The surgical instrument 1110 is further illustrated to include a generally tubular sleeve 1138 surrounding the spindle 1122 in a manner similar to the sleeve 1038 of the first preferred embodiment. The sleeve 1138 is movable between a first position (shown in FIG. 18A) and a second position (shifted to the right from that shown in FIG. 18A). A biasing mechanism such as the coil spring of the first preferred embodiment functions to bias the sleeve 1138 to its first position. To improve the tactile feel received by the user of the surgical instrument 1110 during engagement between the sleeve 1038 and the locking balls 1124, a split ring or an 0ring may be provided in a tapered portion of the sleeve 1138.

When the sleeve 1138 is in its first position, the locking balls 1124 are forced into engagement with the reduced diameter section 1116 of the dissection tool 1112 to thereby inhibit inadvertent withdrawal of the dissection tool 1112 from the generally cylindrical cavity 1120. Further, when the sleeve 1132 is in its first position, the drive balls 1128 are securely engaged with the tapered sides 1114 of the dissection tool 1112 so as to allow the drive balls 1128 to rotate the dissection tool 1112.

When the sleeve 1138 is shifted to its second position, the locking balls 1124 are permitted to radially move within the apertures 1126 to thereby allow withdrawal of the dissection tool 1112 from the generally cylindrical aperture 1120. Further, in the second position of the sleeve 1138, the drive balls 1128 are also aligned with a spherical groove 1134 defined on the inner diameter of the sleeve 1138. The spherical groove 1134 will receive drive balls 1128, preventing the movement of the sleeve to the first position if the user installs a dissecting tool that was not designed for use in this instrument.

Figure 19A:
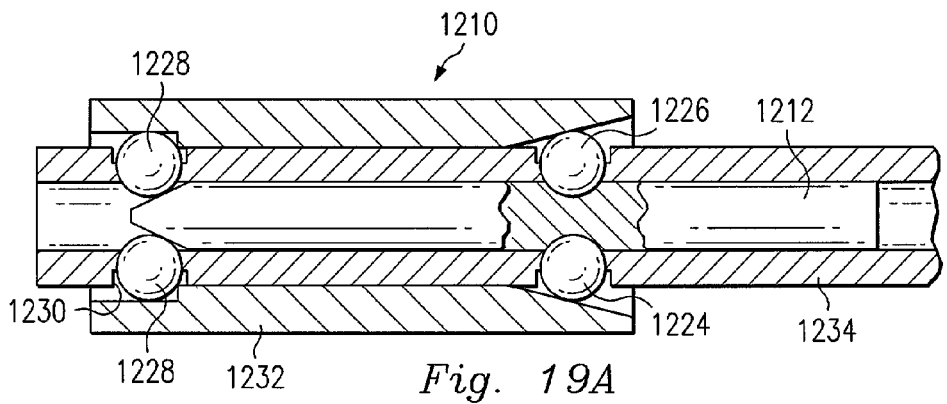
FIG. 19A is a partial cross-sectional side view of another dissection tool coupling assembly according to another aspect of the present invention.
Figure 19B:
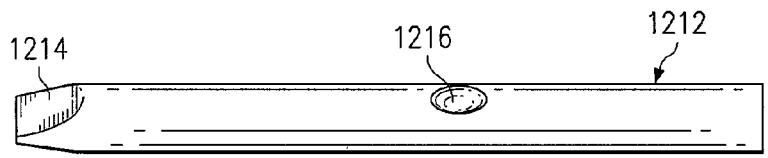
FIG. 19B is a side elevational view of the dissection tool of FIG. 19A.

With reference to FIGS. 19A and 19B, a surgical instrument 1210 for the dissection of bone and other tissue according to the teachings of a further preferred embodiment of the present invention is illustrated. A dissection tool 1212 is secured to a sleeve 1232 in the surgical instrument 1210 in a manner similar to the embodiment shown in FIGS. 18A and 18B. In this regard, the dissection tool 1212 includes two tapered sides 1214 at the distal end of the dissection tool 1212, and two partially spherical recesses 1216 also at the distal end of the dissection tool 1212. The tapered sides 1214 are used to engage two drive balls 1228 which are secured in the radially extending recesses 1230 located in the spindle 1232 and act to align the dissection tool 1212. In addition, the partially spherical recesses 1216 are used to engage two locking balls 1224 which are located in radial extending apertures 1226 in the spindle 1234. The dissection tool 1212 includes a sleeve 1232 which is used to move the locking balls 1224 as well as the drive balls 1228 in such a manner as to secure or release the dissection tool 1212 from the surgical instrument 1210 in a manner similar to that shown in FIG. 18A.

The above description of the invention is merely exemplary in nature and, thus, variations that do not depart from the gist of the invention are intended to be within the scope of the invention. Such variations are not to be regarded as a departure from the spirit and scope of the invention.

What is claimed is:

1. A surgical instrument for the dissection of bone and other tissue, the surgical instrument comprising:
   a rotary drive shaft including a cavity;
   a dissection tool releasably received in said cavity, the dissection tool defining a longitudinal axis extending between a first end and a second end, said first end having a dissection element, said second end having a centrally located aperture extending along said longitudinal axis, the aperture being a blind bore; and
   a male member carried by said rotary drive shaft and extending into the aperture of the dissection tool.

2. The apparatus of claim 1, wherein said dissection tool has a length between said first end and said second end, said centrally located aperture extending only partially along said length.

3. The apparatus of claim 1, further including at least one driving surface disposed adjacent said second end.

4. The apparatus of claim 3, wherein at least a portion of said at least one driving surface and said centrally located aperture are coaxially disposed along said longitudinal axis.

5. The apparatus of claim 4, wherein said at least one driving surface and said centrally located aperture each include distal portions adjacent said first end, said distal portions are substantially co-terminus along said longitudinal axis.

6. The apparatus of claim 3, wherein said cavity is substantially hexagonal in cross-section and wherein said at least one driving surface is substantially hexagonal in cross-section, said driving surface corresponding in size to said cavity such that said cavity cooperates with said driving surface to rotate said dissection element.

7. The apparatus of claim 3, wherein said second end has a generally cylindrical cross-section that is interrupted by at least one longitudinally extending groove formed in said dissection tool, said groove defining at least one driving shoulder.

8. The apparatus of claim 7, further including at least two longitudinal extending grooves.

9. The apparatus of claim 1, further including at least one gripper moveably associated with said rotary drive shaft and disposed adjacent said cavity, said gripper movable from a locked position coupled to said dissection tool and an unlocked position decoupled from said dissection tool.

10. The apparatus of claim 1, wherein said male member has a substantially circular cross-section.

11. The apparatus of claim 10, wherein said male member is substantially cylindrical.

12. A surgical instrument for the dissection of bone and other tissue, the surgical instrument comprising:
a rotary drive shaft including a cavity,
a dissection tool releasably receivable in said cavity, the dissection tool defining a longitudinal axis extending between a first end and a second end, said first end having a dissection surface, said second end having a receiving means for axial alignment along the longitudinal axis; and
a means for engaging said receiving means for alignment carried by said rotary drive shaft cooperating therewith to longitudinally align said dissection tool with said rotary drive shaft.

13. The apparatus of claim 12, wherein said receiving means for axial alignment includes a cavity formed in said dissection tool along said longitudinal axis.

14. A powered surgical instrument for the dissection of bone and other tissue having a hand piece cooperable with a dissection tool having a longitudinal axis, the hand piece comprising:
a hand piece body having an internal cavity;
a motor for supplying rotary force disposed within said internal cavity, said motor including a rotor shaft having an axis of rotation; and
a coupling assembly having a proximal portion and an opposite distal portion, said proximal portion adapted for coupling with said rotor shaft, said distal portion including a channel for receiving a portion of the dissection tool and also including an axial alignment surface disposed on a projection in said channel, said axial alignment surface urging the dissection tool to substantially align the longitudinal axis with said axis of rotation.

15. The apparatus of claim 14, wherein said motor is pneumatically powered.

16. A powered surgical instrument for the dissection of bone and other tissue having a hand piece cooperable with a dissection tool having a longitudinal axis, the hand piece comprising:

a hand piece body having an internal cavity;
a motor for supplying rotary force disposed within said internal cavity, said motor including a rotor shaft having an axis of rotation; and
a coupling assembly having a proximal portion and an opposite distal portion, said proximal portion adapted for coupling with said rotor shaft, said distal portion including a channel for receiving a portion of the dissection tool and also including an axial alignment surface disposed adjacent said channel, said axial alignment surface urging the dissection tool longitudinal axis into substantial alignment with said axis of rotation, wherein said axial alignment surface is defined on a projection extending into said channel in alignment with said axis of rotation.

17. A surgical tool for dissection of tissue, comprising:
an elongated shaft having a first end, an opposite second end, an external surface and a longitudinal axis extending between said first end and said opposite second end;
a dissecting element disposed proximal said first end; and
at least one blind bore extending within said external surface and in substantial alignment with said longitudinal axis, said at least one blind bore having an opening disposed adjacent said opposite second end, said shaft further includes at least one torque transmission surface disposed adjacent said opposite second end on said external surface, said torque transmission surface adapted to cooperate with a coupling member of a powered shaft to thereby transmit rotary force to said dissecting element, wherein said blind bore and said torque transmission surface each include distal portions, said distal portions substantially co-terminus along said longitudinal axis.

18. A surgical dissection tool, comprising:
an elongated shaft having a first end and an opposite second end and a longitudinal axis extending therebetween;
a dissection surface disposed adjacent said first end;
an external drive surface disposed adjacent said second end; and
an internal alignment passage adjacent said second end and coaxially disposed with said external drive surface along said longitudinal axis, the alignment passage being configured to not provide a fluid coolant to the dissection surface, wherein said drive surface includes multiple planes defining a substantially cylindrical drive surface.

19. A surgical dissection tool, comprising:
an elongated shaft having a first end and an opposite second end and a longitudinal axis extending therebetween;
a dissection surface disposed adjacent said first end;
an external drive surface disposed adjacent said second end; and
an internal alignment passage adjacent said second end and coaxially disposed with said external drive surface along said longitudinal axis, the alignment passage being configured to not provide a fluid coolant to the dissection surface, wherein said drive surface is substantially cylindrical and is hexagonal in cross-section.

20. A surgical dissection tool, comprising:
an elongated shaft having a first end and an opposite second end and a longitudinal axis extending therebetween;
a dissection surface disposed adjacent said first end;
an external drive surface disposed adjacent said second end; and an internal alignment passage adjacent said second end and coaxially disposed with said external drive surface along said longitudinal axis, the alignment passage being configured to not provide a fluid coolant to the dissection surface, wherein said elongated shaft is configured for mating engagement with a powered coupling assembly having a powered shaft with a shaft longitudinal axis and driving surfaces for transmitting torque to a tool shaft, wherein said alignment passage includes means for alignment with the shaft longitudinal axis and means for rotational alignment with the driving surfaces.

21. A surgical dissection tool configured for coupling with a driving member of a motor, the driving member having an axis of rotation, the surgical dissection tool comprising:
 an elongated shaft having a first end, an opposite second end, an external surface and a longitudinal axis extending between said first end and said opposite second end;
 a dissecting surface disposed proximal said first end;
 at least one driving surface adapted to receive rotational force from a corresponding driving member, said driving surface disposed adjacent said second end; and
 at least one alignment surface formed adjacent said second end, said alignment surface configured to cooperate with at least one surface of the driving member to substantially align said longitudinal axis with said axis of rotation,
 wherein said at least one driving surface includes three or more driving surfaces.

22. The apparatus of claim 21, wherein said at least one alignment surface is disposed internally within the tool shaft.

23. The apparatus of claim 22, wherein said alignment surface is disposed co-axially with said at least one driving surface.

24. The apparatus of claim 22, wherein said at least one alignment surface is substantially cylindrical.

25. A surgical dissection tool shaft support for cooperation with a motor housing, the tool shaft support comprising:
 a body having an exterior surface and an internal channel adapted to receive a tool shaft and defining a longitudinal axis therethrough;
 said exterior surface including
  a first portion adapted for connection to a motor housing, said first portion having a first diameter,
  a second portion adjacent said first portion, having bearings for supporting the tool shaft,
  a first taper between said first portion and said second portion, and
  a distal taper extending substantially between said second portion and said internal channel;
 said first portion and said first taper defining a first transition; and
 said second portion and said distal taper defining a second transition, wherein said first transition and said second transition are located along a sight line, said sight line disposed at angle with respect to said longitudinal axis of approximately 10°.

26. The apparatus of claim 25, wherein said internal channel includes an internal taper configuration decreasing in diameter from the distal end axially disposed adjacent said distal taper.

27. A surgical instrument for the dissection of bone and other tissue that may be assembled by a user, said instrument comprising:
 a hand piece having a proximal end and an opposite distal end, said distal end having a tapered external surface and a recess formed in said tapered surface;
 an attachment assembly having an internal chamber adapted to receive at least a portion of said distal end in an interference fit, said internal chamber including an internal groove; and
an expandable member partially carried within said internal groove, wherein said expandable member is compressed into said internal groove by contact with said tapered external surface and, when aligned with said recess, expands into said recess to produce tactile feedback to the user indicating proper alignment.

28. The apparatus of claim 27, wherein tapered surface is generally conical.

29. The apparatus of claim 28, said recess is an annular recess.

30. The apparatus of claim 29, wherein said distal end includes a substantially non-cylindrical portion adjacent said tapered surface.

31. The apparatus of claim 27, wherein said internal groove is an annular internal groove.

* * * * *